(12) United States Patent
Bonomo et al.

(10) Patent No.: US 9,949,995 B2
(45) Date of Patent: Apr. 24, 2018

(54) COMPOSITIONS AND METHODS OF TREATING OF BACTERIAL INFECTIONS WITH β-LACTAMASE INHIBITORS

(71) Applicant: CASE WESTERN RESERVE UNIVERSITY, Cleveland, OH (US)

(72) Inventors: Robert Bonomo, Cleveland, OH (US); Fabio Prati, Modena MO (IT); Emilia Caselli, Modena MO (IT); Chiara Romagnoli, Modena MO (IT)

(73) Assignee: Case Western Reserve University, Cleaveland, OH (US)

(*) Notice: Subject to any disclaimer, the term of this patent is extended or adjusted under 35 U.S.C. 154(b) by 0 days.

(21) Appl. No.: 15/257,706

(22) Filed: Sep. 6, 2016

(65) Prior Publication Data
US 2017/0065626 A1 Mar. 9, 2017

Related U.S. Application Data

(60) Provisional application No. 62/214,531, filed on Sep. 4, 2015, provisional application No. 62/256,442, filed on Nov. 17, 2015.

(51) Int. Cl.
*A61K 31/69* (2006.01)
*A61K 31/407* (2006.01)
*A61K 31/546* (2006.01)

(52) U.S. Cl.
CPC ............ *A61K 31/69* (2013.01); *A61K 31/407* (2013.01); *A61K 31/546* (2013.01)

(58) Field of Classification Search
USPC .......................................... 514/64, 330, 340
See application file for complete search history.

(56) References Cited

FOREIGN PATENT DOCUMENTS

WO    WO2013053372 A1 *  4/2013  .............. C07F 5/02

OTHER PUBLICATIONS

Silver; Clinical Microbiology Reviews; Jan. 2011, 24(1), 71-109.*

* cited by examiner

*Primary Examiner* — Pancham Bakshi
(74) *Attorney, Agent, or Firm* — Tarolli, Sundheim, Covell & Tummino LLP

(57) ABSTRACT

A method of treating a bacterial infection in a subject in need thereof includes administering to the subject therapeutically effective amounts of at least one β-lactam antibiotic and at least one triazolylmethyl boronic acid.

3 Claims, 1 Drawing Sheet

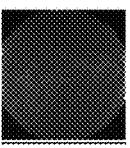

COMPOSITIONS AND METHODS OF TREATING OF BACTERIAL INFECTIONS WITH β-LACTAMASE INHIBITORS

RELATED APPLICATION

This application claims priority from U.S. Provisional Application No. 62/214,531, filed Sep. 4, 2015 and 62/256,442 filed Nov. 17, 2015, the subject matter of which are incorporated herein by reference in their entirety.

GOVERNMENT FUNDING

This invention was made with government support under Grant Nos. R01AI100560, and R01 AI063517 awarded by The National Institute of Allergy and Infectious Diseases of the National Institutes of Health. The United States government has certain rights to the invention.

FIELD OF THE INVENTION

This application relates to compounds, compositions and methods for treating bacterial infections, as well as to antibiotics and β-lactamase inhibitors to treat resistant infections.

BACKGROUND

Bacterial production of β-lactamases represents the most clinically concerning mechanism of resistance to β-lactam antibiotics in Gram negative bacteria. The emergence of many recent β-lactamase variants (>1600 new enzymes) jeopardizes the efficacy of both the latest developed antibiotics and the combination of β-lactam/β-lactam inhibitor (BLI) (e.g., the formulation ampicillin and clavulanic acid are ineffective against bacteria expressing inhibitor resistant TEM and SHV β-lactamases). At the moment, boronic acids transition state inhibitors (BATSIs) represent a class of BLIs in development, as shown by the advancement of a combination of a boronic acid inhibitor (RPX7009 currently developed by the Medicines Company) with meropenem (a carbapenem), in clinical trials (Clinical Trials Phase 1 registration number NCT01897779, RPX7009 is joined with RPX2014). Carbavance (meropenem/RPX7009) is particularly targeted against KPC (*Klebsiella pneumoniae* carbapenemase)-producing carbapenem-resistant Enterobacteriaceae (CRE).

α-Amidomethaneboronic acid is a recurring core-structure in biologically active and important boron-containing compounds. α-Amidomethaneboronate unit is the basic structure of peptidoboronic acids, a class of peptidomimetics largely explored to target different clinically relevant proteases. For example, the anticancer Velcade is a dipeptidyl boronic acid (Phe-boroLeu) acting as proteasome inhibitor, while derivatives of the type Val-boroPro or Pro-boroAla have been investigated as dipeptidyl peptidase-4 inhibitors for the treatment of diabetes. The same skeleton is part also of simpler acylamidomethaneboronic acids, reported as subtilisin and α-chymotrypsin inhibitors and used as fluorescent carbohydrate sensors.

SUMMARY

Embodiments described herein relate to method of treating a bacterial infection in a subject in need thereof. The method includes administering to the subject therapeutically effective amounts of at least one β-lactam antibiotic and at least one triazolylmethyl boronic acid β-lactamase inhibitor.

In some embodiments, the triazolylmethyl boronic acid is a compound of the formula:

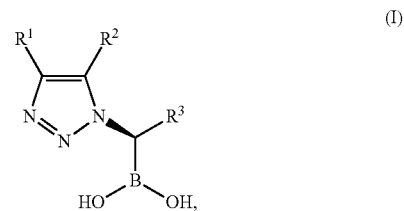

(I)

wherein, $R^1$, $R^2$, and $R^3$ are the same or different and are each independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, sulfanamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, —$SO_2NR'_2$ (wherein R' is independently H, aryl or alkyl), phosphono, phosphonato, phosphinato, phospho, phosphino, polyalkyl ethers, phosphates, phosphate esters, and combinations thereof, and pharmaceutically acceptable salts thereof.

In other embodiments, the triazolylmethyl boronic acid is a compound of the formula:

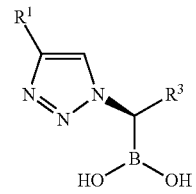

wherein $R^1$ and $R^3$ are the same or different and are each independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, sulfanamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, —$SO_2NR'_2$ (wherein R' is independently H, aryl or alkyl), phosphono, phosphonato, phosphinato, phospho, phosphino, polyalkyl ethers, phosphates, phosphate esters, and combinations thereof, and pharmaceutically acceptable salts thereof.

In still other embodiments, the triazolylmethyl boronic acid is selected from the group consisting of:

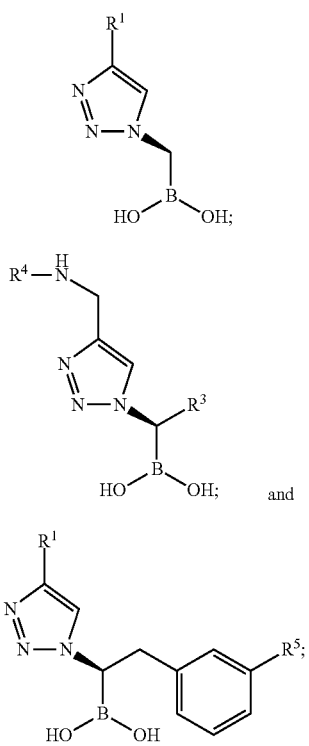

(III)

(IV)

(V)

wherein $R^1$, $R^3$, $R^4$, and $R^5$ are the same or different and are each independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)$C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, sulfanamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, —$SO_2NR'_2$ (wherein R' is independently H, aryl or alkyl), phosphono, phosphonato, phosphinato, phospho, phosphino, polyalkyl ethers, phosphates, phosphate esters, and combinations thereof, and pharmaceutically acceptable salts thereof.

In some embodiments, $R^1$, $R^3$, $R^4$, and $R^5$ are same or different and are each independently selected from the group consisting hydrogen, halogen, —$CX^a_3$, —CN, —$SO_2Cl$, —$SO_pR^6$, —$SO_qNR^7R^8$, —$NHNH_2$, —$ONR^9R^{10}$, —$NHC=(O)NHNH_2$, —$NHC=(O)NR^{11}R^{12}$, —$N(O)_r$, —$NR^{13}R^{14}$, —$C(O)R^{15}$, —$C(O)$—$OR^{16}$, —$C(O)NR^{17}R^{18}$, —$OR^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, the symbols q and r are independently 1 or 2, the symbol p is independently an integer from 0 to 4, the symbol $X^a$ is Cl, Br, I, or F, and pharmaceutically acceptable salts thereof. In other embodiments, the bacterial infection is a β-lactam antibiotic resistant gram negative bacterial infection.

The β-lactam antibiotic can include at least one of amoxicillin, ampicillin, azlocillin, mezlocillin, hetacillin, bacampicillin, carbenicillin, sulbenicillin, ticarcillin, piperacillin, mecillinam, methicillin, ciclacillin, oxacillin, cloxacillin, dicloxacillin, nafcillin, cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, cefinenoxime, cefmetazole, cephaloglycin, cefonicid, cefodizime, cefpirome, ceftazidime, ceftriaxone, cefpiramide, cefozopran, cefepime, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbacef, latamoxef, CXA-101, imipenem, meropenem, biapenem, panipenem, ertapenem, doripenem, aztreonam, carumonam, and pharmaceutically acceptable salts.

BRIEF DESCRIPTION OF THE DRAWINGS

FIG. 1 illustrates images of culture plates of *E. coli* DH10B or DC-2 (hyperpermeable strain) harboring cloned b-lactamase (KPC-2, ADC-7, PDC-3) in pBCSK-expression vector treated with an antibiotic (imipenem, IMI or ceftazidime, CTZ) and a triazolylmethyl boronic acid β-lactamase inhibitor described herein.

DETAILED DESCRIPTION

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.,", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substitutents, e.g., sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl)N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analogue" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles,"

"heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and al kylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate. The term sulfoxide refers to a sulfur attached to 2 different carbon atoms and one oxygen and the S—O bond can be graphically represented with a double bond (S=O), a single bond without charges (S—O) or a single bond with charges [S(+)—O(−)].

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—CN), isocyano (—$N^+C^-$), cyanato (—O—CN), isocyanato (—$ON^+C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)($OH)_2$), phosphonato (—P(O)($O^-)_2$), phosphinato (—P(O)($O^-$)), phospho (—$PO_2$), and phosphino (—$PH_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties, such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

It should be noted that throughout the application that alternatives are written in Markush groups, for example, each substituent position in a compound that contains more than one possible substituent. It is specifically contemplated that each member of the Markush group should be considered separately, thereby comprising another embodiment, and the Markush group is not to be read as a single unit.

Description of compounds described herein are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A "boronic acid", as used herein, means a substituent with the structure —$B(OH)_2$. The term "boronic ester" is used according to its plain ordinary meaning and refers to a compound formed between a boronic acid and one or more alcohols (e.g., boronic acid pinacol ester or boronic acid pinanediol ester).

The term "cephalosporin" is used according to its plain ordinary meaning and refers to compounds that are derived from or related to 7-aminocephalosporanic acid, including modifications wherein functional groups or sidechains of the core 7-aminocephalosporanic acid group are modified or removed. The term "cephems" refers to the group of antibiotics comprising the cephalosporins and cephamycins.

The term "penicillin" is used according to its plain ordinary meaning and refers to compounds that are derived from or related to 6-aminopenicillanic acid, including modifications wherein functional groups or sidechains of the core 6-aminopenicillanic acid group are modified or removed.

The term "carbapenem" is used according to its plain ordinary meaning and refers to a class of beta lactam containing antibiotics including imipenem, meropenem, ertapenem, doripenem, panipenem, betamipron, biapenem, and tebipenem.

Cephalosporins are well known to be categorized into generations. When referring to a generation of cephalosporins herein, each generation is defined as commonly defined in the United States by medical practitioners or reference guides. "First generation cephalosporins" include Cefacetrile (cephacetrile), Cefadroxil (cefadroxyl; Duricef), Cephalexin (cephalexin; Keflex), Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole. "Second generation cephalosporins" include Cefaclor (Ceclor, Distaclor, Keflor, Raniclor), Cefonicid (Monocid), Cefprozil (cefproxil; Cefzil), Cefuroxime (Zefu, Zinnat, Zinacef, Ceftin, Biofuroksym, Xorimax), Cefuzonam, Cefmetazole, Cefotetan, Cefoxitin. The following cephems are also sometimes grouped with second-generation cephalosporins: Carbacephems: loracarbef (Lorabid); Cephamycins: cefbuperazone, cefmetazole (Zefazone), cefminox, cefotetan (Cefotan), cefoxitin (Mefoxin). "Third generation cephalosporins" include Cefcapene, Cefdaloxime, Cefdinir (Zinir, Omnicef, Kefnir), Cefditoren, Cefetamet, Cefixime (Zifi, Suprax), Cefmenoxime, Cefodizime, Cefotaxime (Claforan), Cefovecin (Convenia), Cefpimizole, Cefpodoxime (Vantin, PECEF), Cefteram, Ceftibuten (Cedax), Ceftiofur, Ceftiolene, Ceftizoxime (Cefizox), Ceftriaxone (Rocephin), Cefoperazone (Cefobid), Ceftazidime (Fortum, Fortaz). The following cephems are also sometimes grouped with third-generation cephalosporins: Oxacephems: latamoxef (moxalactam). "Fourth generation cephalosporins" include Cefclidine, Cefepime (Maxipime), Cefluprenam, Cefoselis, Cefozopran, Cefpirome (Cefrom), Cefquinome, Oxacephems, flomoxef. "Fifth generation cephalosporins" include Ceftobiprole, Ceftaroline. Additional cephems include Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, Cefuracetime.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being, or improving the effectiveness of a method or compound administered to the patient for the purpose of treating the same disease (e.g., improving the effectiveness of an agent (i antibiotic, antimicrobial, antibacterial) administered for treatment of a disease). The treatment or amelioration of symptoms can be based on objective or subjective parameters; including the results of a physical examination, neuropsychiatric exams, and/or a psychiatric evaluation. For example, the certain methods presented herein successfully treat infectious diseases by, without being limited by mechanism, decreasing the growth, survival, and/or replication of infectious agents (e.g., bacteria), decreasing the growth, survival, and/or replication of infectious agents (e.g., bacteria) resistant to one or more antibiotics (e.g., penicillins, cephalosporins, β-lactam containing compounds, β-lactam containing antibiotics/β-lactam antibiotics), sensitizing infectious agents to one or more antibiotics (e.g., β-lactam containing compounds or β-lactam containing antibiotics/β-lactam antibiotics), inhibiting bacterial cell wall synthesis, inhibiting β-lactamase activity. The term "treating," and conjugations thereof, include prevention of an injury, pathology, condition, or disease.

The terms "antibiotic" and "antibacterial" are used according to their plain ordinary meaning, as would be understood by a medical professional, and refer to compounds that kill or slow the growth of bacteria. The term "antimicrobial" is used according to its plain ordinary meaning, as would be understood by a medical professional, and refers to compounds that kill or slow the growth of microbes (e.g., bacteria, viruses, fungi, certain parasites). An "effective amount" is an amount sufficient to accomplish a stated purpose (e.g., achieve the effect for which it is administered, treat a disease, reduce enzyme activity, reduce one or more symptoms of a disease or condition, reduce the level of β-lactamase activity, sensitize an infectious agent to a second therapeutic agent (e.g., antibiotic, β-lactam containing compound, β-lactam containing antibiotic/β-lactam antibiotic, penicillin, cephalosporin). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist or compound required to decrease the activity of an enzyme (e.g., β-lactamase) relative to the absence of the antagonist or compound. A "function disrupting amount," as used herein, refers to the amount of antagonist or compound required to disrupt the function of an enzyme or protein (e.g. β-lactamase) relative to the absence of the antagonist or compound. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g., chemical compounds including biomolecules, proteins, or cells) to become sufficiently proximal to react, interact or physically touch. It should be appreciated, however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein (e.g., β-lactamase). In some embodiments, the protein may be an enzyme. In some embodiments, the enzyme may be a β-lactamase. In some embodiments, the β-lactamase may be a class A β-lactamase). In some embodiments, the β-lactamase may be a class B β-lactamase). In some embodiments, the β-lactamase may be a class C β-lactamase). In some embodiments, the β-lactamase may be a class D β-lactamase). In some embodiments, contacting includes allowing a compound described herein to interact with a protein or enzyme that promotes the hydrolysis of β-lactam containing compounds. In some embodiments, contacting includes allowing a compound described herein to interact with an enzyme active site through specific amino acids (e.g., side chain atom or backbone atom). In some embodiments, contacting includes allowing a compound described herein to interact with an enzyme active site through specific amino acids identified through an x-ray crystal structure of the enzyme, or a similar or homologous enzyme, interacting with a substrate or compound described herein.

The terms "β-lactamase" or "β-lactamase" or "β-lactamase enzyme", are used interchangeably and according to their plain ordinary meaning and refer to an enzyme or enzymes that catalyze the hydrolysis of β-lactam rings. β-lactamase enzymes include those enzymes identified by the Enzyme Commission number EC 3.5.2.6. β-lactamases include the enzymes identified by the UniProt numbers P05193, AMPC_CITFR; P00811, AMPC_ECOLI; P05364, AMPC_ENTCL; Q48743, AMPC_LYSLA; P94958, AMPC_MORMO; O69773, AMPC_PROST; P24735, AMPC_PSEAE; P85302, AMPC_PSEFL; O05465, AMPC_PSYIM; P18539, AMPC_SERMA; P45460, AMPC_YEREN; Q9S424, BLA13_KLEPN; P67920, BLA1_ACTPL; Q44056, BLA1_AERHY; P10424, BLA1_BACCE; P28018, BLA1_BACMY; P0AD63, BLA1_ECOLX; P18251, BLA1_ENTCL; P67918, BLA1_HAEIF; P0AD64, BLA1_KLEPN; Q59514, BLA1_MORCA; P67919, BLA1_PASHA; P52700, BLA1_STEMA; Q03680, BLA1_STRCI; Q9S169, BLA24_ECOLX; Q9AHN9, BLA29_KLEPN; P10425, BLA2_BAC17; P04190, BLA2_BACCE; P0A9Z7, BLA2_ECOLX; P0A9Z8, BLA2_KLEPN; P0A9Z9, BLA2_KLEPO; P0AA00, BLA2_SALTY; P96465, BLA2_STEMA; P14560, BLA2_STRCI; Q93LM8, BLA34_ECOLX; P06548, BLA3_BACCE; P30896, BLA3_KLEPN; Q848S4, BLA46 KLEOX; P37323, BLA4_KLEPN; P0A3M1, BLA5 KLEPN; P0A3M2, BLA5_PSEAE; P96348, BLA6_KLEPN; O08337, BLA8_ECOLX; O08498, BLAB1_FLAME; Q9RB01, BLAB2_FLAME; Q9K303, BLAB3_FLAME; Q9XBN7, BLAB4_FLAME; Q9KJA9, BLAB5_FLAME; Q9KJB0, BLAB6_FLAME; Q9KJA8, BLAB7_FLAME; Q9KJA7, BLAB8 FLAME; P26918, BLAB_AERHY; P14488, BLAB_BACCE; P25910, BLAB_BACFR; P52664, BLAB_ PROVU; P52699, BLAB_SERMA; Q44674, BLAC_BACAM; P00809, BLAC_BACCE; P00808, BLAC_BACLI; P39824, BLAC_BACSU; Q45726, BLAC_BACTU; P30898, BLAC_BACUN; P30899, BLAC_BACVU; P22390, BLAC_C1TDI; P05192, BLAC_KLEPN; P0A517, BLAC_MYCBO; A5U493, BLAC_MYCTA; P0C5C1, BLAC_MYCTU; Q9EZQ7, BLAC_NOCAS; Q5YXD6, BLAC_NOCFA; Q06316, BLAC_NOCLA; P30897, BLAC_PROMI; P80298, BLAC_PROVU; P14171, BLAC_RHOCA; P80545, BLAC_SERFO; P00807, BLAC_STAAU; P14559, BLAC_STRAL; P10509, BLAC_STRAU; P35391, BLAC_STRBA; Q06650, BLAC_STRCE; P35392, BLAC_STRFR; P81173, BLAC_STRGR; P35393, BLAC_STRLA; Q01166, BLAC_YEREN; Q59517, BLAF_MYCFO; C7C422, BLAN1_KLEPN; P52663, BLAN_ENTCL; P52682, BLAN_SERMA; P62593, BLAT_ECOLX; Q48406, BLAT_KLEOX; P62594, BLAT_SALTI; P28585, BLC1_ECOLX; P74841, BLC2_SALTY; P37322, BLC3_PSEAE; Q51355, BLC4_PSEAE; O33807, BLC4_SALTY; O65975, BLCS_SALTY; O65976, BLC6_SALTY; P81781, BLC6_VIBCH; P37321, BLEI_PSEAE; Q848S6, BLKPC_KLEOX; Q9F663, BLKPC_KLEPN; Q00983, BLLI_PSEAE; P14489, BLO10_PSEAE; Q06778, BLO11_PSEAE; Q51574, BLO15_PSEAE; O07293, BLO18_PSEAE; Q9R976, BLO19_PSEAE; P13661, BLO1_ECOLX; P22391, BLO1_KLEOX; O84955, BLO20_PSEAE; P0A1V9, BLO2 ECOLX; P23954, BLO2_KLEOX; P0A1V8, BLO2_SALTY; Q51429, BLO3_PSEAE; Q00982, BLOS_PSEAE; P35695, BLO7_ECOLX; P0A3M4, BLO9_ENTAE; P0A3M3, BLO9_KLEPN; Q03170, BLP1_PSEAE; P16897, BLP4_PSEAE; Q47066, BLT1_ECOLX; O69395, BLT2_ECOLX; P0AEB2, DACA_ECOLI; Q9ZMM1, HCPA_HELPJ; O25001, HCPA_HELPY; O25103, HCPB_HELPY; Q9ZKB5, HCPC_HELPJ; O25728, HCPC_HELPY; Q9ZMSO, HCPD_HELPJ; O24968, HCPD_HELPY; Q9ZMJ9, HCPE_HELPJ; O25021, HCPE_HELPY; Q02940, PENA_BURM1; or P54427, YBXI_BACSU.

The term "inhibition", "inhibit", "inhibiting" and the like in reference to a protein-inhibitor (e.g., compound) interaction means negatively affecting (e.g., decreasing) the activity or function of the protein (e.g., decreasing the hydrolysis of β-lactam containing antibiotics) relative to the activity or function of the protein in the absence of the inhibitor (e.g., compound). In some embodiments inhibition refers to reduction of a disease or symptoms of disease. In some embodiments, inhibition refers to a reduction in the presence of a disease-related agent (e.g., an infectious agent, infectious agent resistant to one or more antibiotics, bacterium, bacterium resistant to one or more antibiotics). Thus, inhibition includes, at least in part, partially or totally blocking stimulation, decreasing, preventing, or delaying activation, or inactivating, desensitizing, or down-regulating signal transduction or enzymatic activity or the amount of a protein. Similarly an "inhibitor" is a compound that inhibits bacterial survival, growth, or replication, e.g., by binding, partially or totally blocking, decreasing, preventing, delaying, inactivating, desensitizing, or down-regulating signal transduction or enzymatic activity (e.g., activity responsible for hydrolyzing β-lactam containing compounds).

The term "modulator" refers to a composition that increases or decreases the level of a target molecule or the function of a target molecule (e.g., a target may be a β-lactamase and the function in a disease state of a β-lactamase, may be to hydrolyze therapeutic compounds such as β-lactam containing antibiotics). In some embodiments, a β-lactamase modulator is a compound that reduces the activity of a β-lactamase. A β-lactamase modulator may reduce an enzyme activity that results in a reduction of the amount of β-lactamase activity and reduces the amount of hydrolyzed β-lactam containing compounds or hydrolyzed β-lactam containing antibiotics produced by β-lactamases. In some embodiments, a β-lactamase modulator is a compound that reduces the severity of one or more symptoms of an infectious disease.

"Patient" or "subject in need thereof" refers to a living organism suffering from or prone to a condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refers to a state of being or health status of a patient or subject capable of being treated with the compounds or methods provided herein. In some embodiments, the disease is a disease related to (e.g., caused by) an infectious agent (e.g., bacteria) Examples of diseases, disorders, or conditions include, but are not limited to, infectious diseases, bacterial infectious diseases, nosocomial infections, nosocomial bacterial infections, ventilator associated pneumonias, bacterial blood stream infections, Cutaneous anthrax, Pulmonary anthrax, Gastrointestinal anthrax, Whooping cough, bacterial pneumonia, Lyme disease, Brucellosis, Acute enteritis, Community-acquired respiratory infection, Nongonococcal urethritis (NGU), Lymphogranuloma venereum (LGV), Trachoma, Inclusion conjunctivitis of the newborn (ICN), Psittacosis, Botulism, Pseudomembranous colitis, Gas gangrene, Acute food poisoning, Anaerobic cellulitis, Tetanus, Diphtheria, Nosocomial infections, Urinary tract infections (UTI), Diarrhea, Meningitis in infants, Traveller's diarrhea, Diarrhea in infants, Hemorrhagic colitis, Hemolytic-uremic syndrome, Tularemia, Bacterial meningitis, Upper respiratory tract infections, Pneumonia, bronchitis, Peptic ulcer, gastric carcinoma, gastric B-cell lymphoma, Legionnaire's Disease, Pontiac fever, Leptospirosis, Listeriosis, Leprosy (Hansen's disease), *Tuberculosis, Mycoplasma* pneumonia, Gonorrhea, Ophthalmia neonatorum, Septic arthritis, Meningococcal disease, Waterhouse-Friderichsen syndrome, *Pseudomonas* infection, Bacteremia, endocarditis, Rocky mountain spotted fever, Typhoid fever type salmonellosis (dysentery, colitis), Salmonellosis, gastroenteritis, enterocolitis, Bacillary dysentery/Shigellosis, Coagulase-positive staphylococcal infections, Impetigo, Acute infective endocarditis, Septicemia, Necrotizing pneumonia, Toxinoses, Toxic shock syndrome, Staphylococcal food poisoning, Cystitis, Meningitis, septicemia, Endometritis, Opportunistic infections, Acute bacterial pneumonia, Otitis media, sinusitis, Streptococcal pharyngitis, Scarlet fever, Rheumatic fever, erysipelas, Puerperal fever, Necrotizing fasciitis, Syphilis, Congenital syphilis, Cholera, Plague, Bubonic plague, Pneumonic plague, sepsis, Iraq war infection caused by *Acinetobacter baumannii* (i.e. Iraq war-related *Acinetobacter baumannii* infection), skin diseases or conditions, acne, acne vulgaris, keratosis pilaris, acne rosacea, harlequin ichthyosis, xeroderma pigmentosum, keratoses, eczema, rosacea, necrotizing fasciitis, tuberculosis, hospital-acquired pneumonia, gastroenteritis, or bacteremia.

The term "infectious disease" refers to a disease or condition related to the presence of an organism (the agent or infectious agent) within or contacting the subject or patient. Examples include a bacterium, fungus, virus, or other microorganism. A "bacterial infectious disease" is an infectious disease wherein the organism is a bacterium. A "viral infectious disease" is an infectious disease wherein the organism is a virus. An "antibiotic resistant bacterial infectious disease" is an infectious disease wherein the organism is a bacterium resistant to one or more antibiotics effective in treating a disease caused by the non-antibiotic resistant strains of the bacterium. A "penicillin resistant bacterial infectious disease" is an antibiotic resistant bacterial infectious disease wherein the disease is not treated as effectively by a penicillin or penicillin-related compounds as a similar disease caused by a bacterial strain that is not penicillin resistant. A "cephalosporin resistant bacterial infectious disease" is an antibiotic resistant bacterial infectious disease wherein the disease is not treated as effectively by a cephalosporin or cephalosporin-related compounds as a similar disease caused by a bacterial strain that is not cephalosporin resistant. A "β-lactam antibiotic resistant bacterial infectious disease" is a an antibiotic resistant bacterial infectious disease wherein the disease is not treated as effectively by β-lactam containing antibiotics as a similar disease caused by a bacterial strain that is not β-lactam antibiotic resistant. Examples of infectious diseases that may be treated with a compound or method described herein include nosocomial infections, bacteremia, Cutaneous anthrax, Pulmonary anthrax, Gastrointestinal anthrax, Whooping cough, bacterial pneumonia, bacteremia, Lyme disease, Brucellosis, Acute enteritis, Community-acquired respiratory infection, Nongonococcal urethritis (NGU), Lymphogranuloma venereum (LGV), Trachoma, Inclusion conjunctivitis of the newborn (ICN), Psittacosis, Botulism, Pseudomembranous colitis, Gas gangrene, Acute food poisoning, Anaerobic cellulitis, Tetanus, Diphtheria, Nosocomial infections, Urinary tract infections (UTI), Diarrhea, Meningitis in infants, Traveller's diarrhea, Diarrhea in infants, Hemorrhagic colitis, Hemolytic-uremic syndrome, Tularemia, Bacterial meningitis, Upper respiratory tract infections, Pneumonia, bronchitis, Peptic ulcer, gastric carcinoma, gastric B-cell lymphoma, Legionnaire's Disease, Pontiac fever, Leptospirosis, Listeriosis, Leprosy (Hansen's disease), *Tuberculosis, Mycoplasma* pneumonia, Gonorrhea, Ophthalmia neonatorum, Septic arthritis, Meningococcal disease, Waterhouse-Friderichsen syndrome, *Pseudomonas* infection, Bacteremia, endocarditis, Rocky mountain spotted fever, Typhoid fever type salmonellosis (dysentery, colitis), Salmonellosis, gastroenteritis, enterocolitis, Bacillary dysentery/Shigellosis, Coagulase-positive staphylococcal infections: Impetigo, Acute infective endocarditis, Septicemia, Necrotizing pneumonia, Toxinoses, Toxic shock syndrome, Staphylococcal food poisoning, Cystitis, Meningitis, septicemia, Endometritis, Opportunistic infections, Acute bacterial pneumonia, Otitis media, sinusitis, Streptococcal pharyngitis, Scarlet fever, Rheumatic fever, erysipelas, Puerperal fever, Necrotizing fasciitis, Syphilis, Congenital syphilis, Cholera, Plague, Bubonic plague, Pneumonic plague, Iraq war infection caused by *Acinetobacter baumannii* (i.e., Iraq war-related *Acinetobacter baumannii* infection), necrotizing fasciitis, tuberculosis, hospital-acquired pneumonia, gastroenteritis, or sepsis.

"Infectious agent" refers to an organism that is associated with (in or contacting) patients with an infectious disease but not in patients without the infectious disease and wherein contacting a patient without the infectious disease with the organism results in the patient having the infectious disease. In some embodiments, the infectious agent associated with a disease that may be treated by the compounds and/or methods described herein is a bacterium. In some embodiments, the bacteria is of a genera selected from *Stenotrophomonas, Clostridium, Acinetobacter, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio, Klebsiella, Enterobacter, Citrobacter,* or *Yersinia*. In some embodiments, the bacteria is selected from *Stenotrophomonas maltophilia, Clostridium difficile, Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli,* Enterotoxigenic *Escherichia coli* (ETEC), Enteropathogenic *E. coli, E. coli* O157:H7, *Francisella tularensis, Haemophilus influenzae, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Klebsiella pneumoniae, Enterobacter cloacae, Citrobacter freundii, Acinetobacter baumannii,* or *Yersinia pestis*. In some embodiments, the bacteria is gram negative. In some embodiments, the bacteria is gram positive.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Embodiments described herein relate to compositions and methods of inhibiting β-lactamase activity as well as to compositions and methods of treating bacterial infections, such as β-lactam antibiotic resistant bacterial infections, in a subject in need thereof. It was found that triazolylmethyl boronic acids can be used to inhibit and/or inactivate β-lactamase activity, and particularly, β-lactamase enzymatic function. The triazolylmethyl boronic acid β-lactamase inhibitors are therefore useful in the treatment of bacterial infections in subjects in need thereof alone or in combination with β-lactam antibiotics and/or with other non-β-lactam antibiotics.

In some embodiments, the triazolylmethyl boronic can be a compound of the formula:

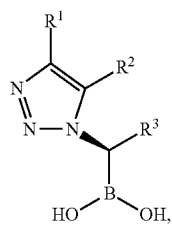

(I)

wherein, $R^1$, $R^2$, and $R^3$ are the same or different and are each independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, sulfanamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, —$SO_2NR'_2$ (wherein R' is independently H, aryl or alkyl), phosphono, phosphonato, phosphinato, phospho, phosphino, polyalkyl ethers, phosphates, phosphate esters, and combinations thereof, and pharmaceutically acceptable salts thereof.

In other embodiments, the triazolylmethyl boronic acid can be a compound of the formula:

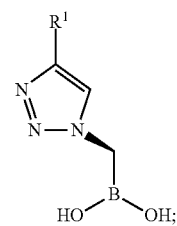

(II)

wherein $R^1$ and $R^3$ are the same or different and are each independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, sulfanamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, —$SO_2NR'_2$ (wherein R' is independently H, aryl or alkyl), phosphono, phosphonato, phosphinato, phospho, phosphino, polyalkyl ethers, phosphates, phosphate esters, and combinations thereof, and pharmaceutically acceptable salts thereof.

In other embodiments, the triazolylmethyl boronic acid is selected from the group consisting of:

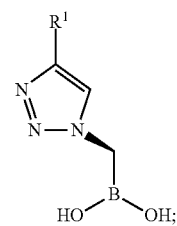

(III)

-continued

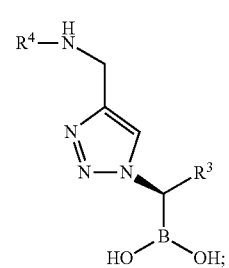
(IV)

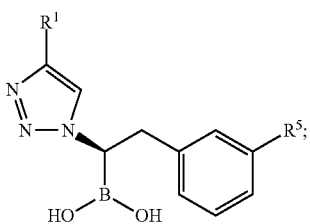
(V)

wherein $R^1$, $R^3$, $R^4$, and $R^5$ are the same or different and are each independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, sulfanamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, —$SO_2NR'_2$ (wherein R' is independently H, aryl or alkyl), phosphono, phosphonato, phosphinato, phospho, phosphino, polyalkyl ethers, phosphates, phosphate esters, and combinations thereof, and pharmaceutically acceptable salts thereof.

In still other embodiments, $R^1$, $R^3$, $R^4$, and $R^5$ are the same or different and are each independently selected from the group consisting hydrogen, halogen, —$CX^a{}_3$, —CN, —$SO_2Cl$, —$SO_pR^6$, —$SO_qNR^7R^8$, —$NHNH_2$, —$ONR^9R^{10}$, —NHC=(O)$NHNH_2$, —NHC=(O)$NR^{11}R^{12}$, —N(O)$_r$, —$NR^{13}R^{14}$, —C(O)$R^{15}$, —C(O)—$OR^{16}$, —C(O)$NR^{17}R^{18}$, —$OR^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, and $R^{19}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, the symbols q and r are independently 1 or 2, the symbol p is independently an integer from 0 to 4, the symbol $X^a$ is Cl, Br, I, or F, and pharmaceutically acceptable salts thereof.

In some embodiments, the triazolylmethyl boronic acid is selected from the group consisting of:

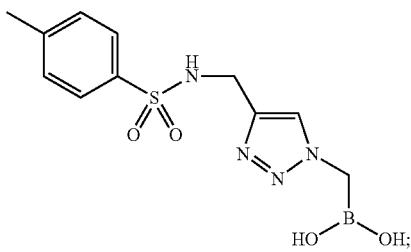

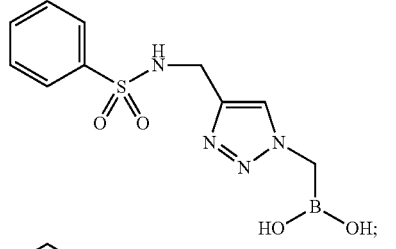

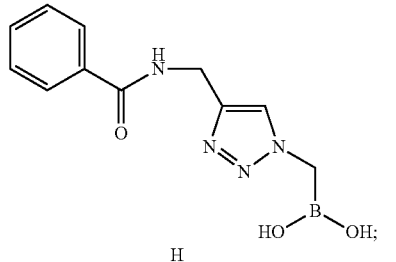

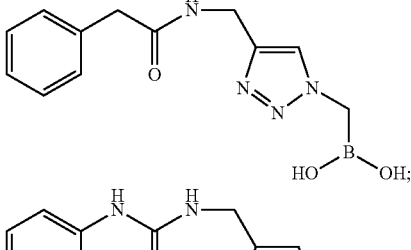

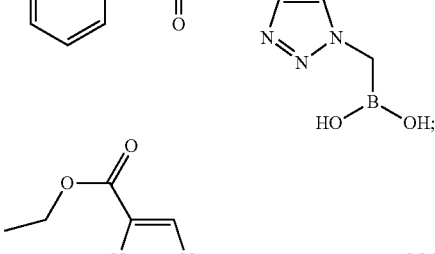

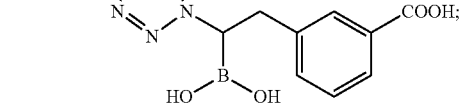

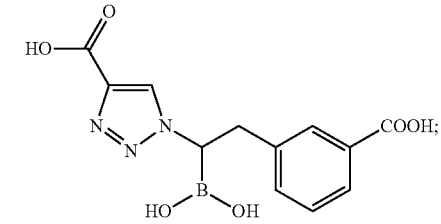

-continued
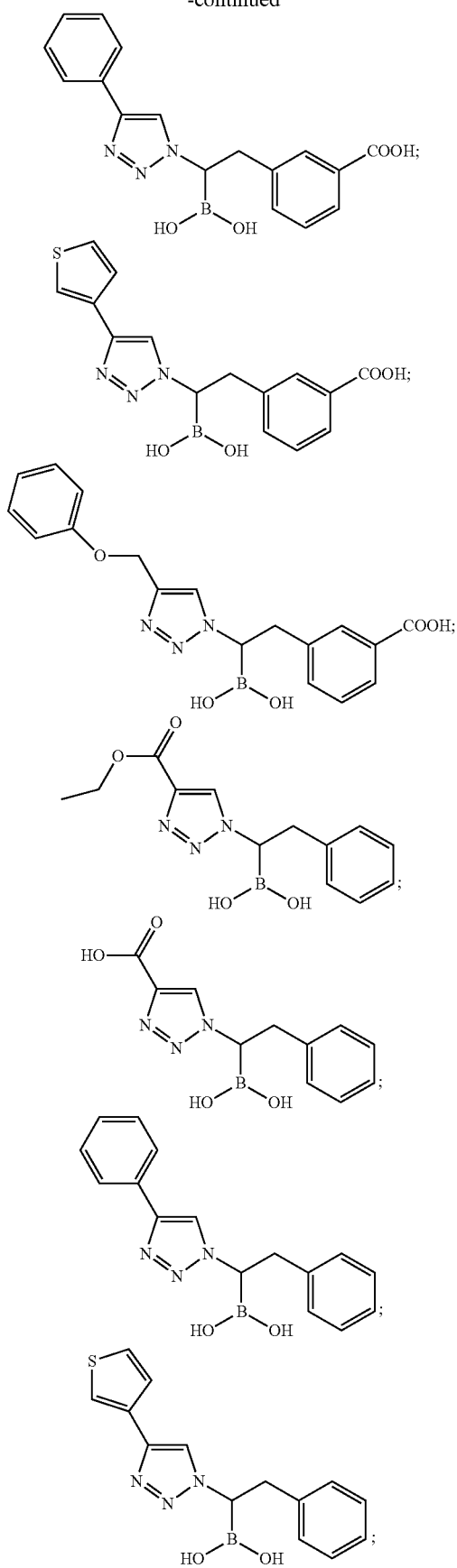
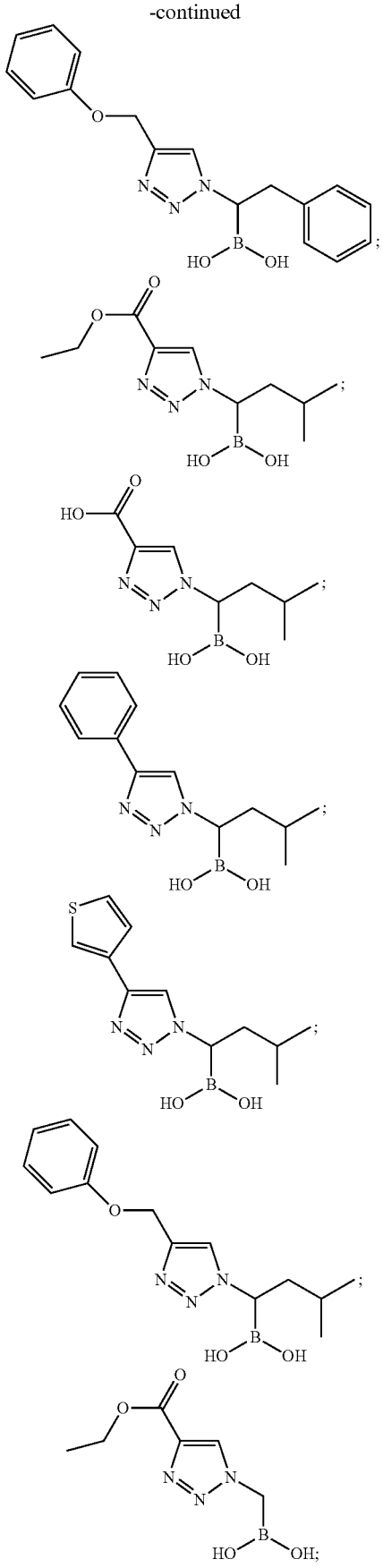

-continued

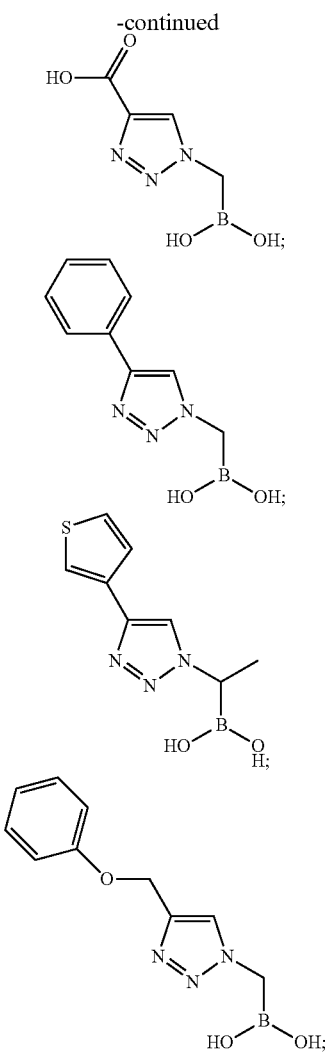

and pharmaceutically acceptable salts thereof.

In some embodiments of a compound described herein (e.g., Formula (I), (II), (III), (IV), or (V)), the compound inhibits the activity of a bacterial β-lactamase. In some embodiments, the bacterial β-lactamase is expressed by a bacterium selected from *Stenotrophomonas maltophilia, Clostridium difficile, Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli,* Enterotoxigenic *Escherichia coli* (ETEC), Enteropathogenic *E. coli, E. coli* O157:H7, *Francisella tularensis, Haemophilus influenzae, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae,* *Klebsiella pneumoniae, Enterobacter cloacae, Citrobacter freundii, Acinetobacter baumannii,* or *Yersinia pestis.* In some embodiments, the bacterial β-lactamase is expressed by a bacterium that is gram negative. In some embodiments, the bacterial β-lactamase is expressed by a bacterium that is gram positive.

In some embodiments, the compounds described herein are not subject to degradation by β-lactamases or upregulation of these enzymes, unlike a classical β-lactam-based inhibitor.

In some embodiments, the triazolylmethyl boronic acids retain substantial inhibition activity against β-lactamases. In other embodiments, they rescue antibiotic resistance when used in combination with third generation antibiotics in bacterial cell cultures.

The triazolylmethyl boronic acids described herein can be used in a method of treating a disease in a patient in need of such treatment. The method can include administering a therapeutically effective amount of a compound as described herein (e.g., Formula (I), (II), (III), (IV), or (V)). In some embodiments, the disease is an infectious disease. In some embodiments, the disease is an infectious disease mediated by a bacterium. In some embodiments, the disease is an infectious disease caused by a bacterium. In some embodiments, the disease is a bacterial infectious disease. In further embodiments, the bacterium is resistant to an antibiotic. In further embodiments, the antibiotic is a β-lactam containing antibiotic. In some embodiments of the method of treating a disease, the bacterium is a gram negative bacterium. In some embodiments of the method of treating a disease, the bacterium is a gram positive bacterium. In some embodiments of the method of treating a disease in a patient in need of such treatment, the method includes administering a therapeutically effective amount of a compound as described herein (e.g., Formula (I), (II), (III), (IV), or (V)).

In further embodiments of the method of treating a disease, the genera of the bacterium is selected from *Stenotrophomonas, Clostridium, Acinetobacter, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio, Klebsiella, Enterobacter, Citrobacter,* or *Yersinia.* In further embodiments of the method of treating a disease, the bacteria is selected from *Stenotrophomonas maltophilia, Clostridium difficile, Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli,* Enterotoxigenic *Escherichia coli* (ETEC), Enteropathogenic *E. coli, E. coli* O157:H7, *Francisella tularensis, Haemophilus influenzae, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Klebsiella pneumoniae, Enterobacter cloacae, Citrobacter freundii, Vibrio* cholerae, Acinetobacter baumannii, or Yersinia pestis. In further embodiments of the method of treating a disease, the bacteria is selected from a β-lactam antibiotic resistant strain of Stenotrophomonas maltophilia, Clostridium difficile, Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Enterotoxigenic Escherichia coli (ETEC), Enteropathogenic E. coli, E. coli O157:H7, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Klebsiella pneumoniae, Enterobacter cloacae, Citrobacter freundii, Acinetobacter baumannii or Yersinia pestis. In some embodiments of the method of treating a disease, the disease is selected from Cutaneous anthrax, Pulmonary anthrax, Gastrointestinal anthrax, Whooping cough, bacterial pneumonia, Lyme disease, Brucellosis, Acute enteritis, Community-acquired respiratory infection, Nongonococcal urethritis (NGU), Lymphogranuloma venereum (LGV), Trachoma, Inclusion conjunctivitis of the newborn (ICN), Psittacosis, Botulism, Pseudomembranous colitis, Gas gangrene, Acute food poisoning, Anaerobic cellulitis, Tetanus, Diphtheria, Nosocomial infections, Urinary tract infections (UTI), Diarrhea, Meningitis in infants, Traveller's diarrhea, Diarrhea in infants, Hemorrhagic colitis, Hemolytic-uremic syndrome, Tularemia, Bacterial meningitis, Upper respiratory tract infections, Pneumonia, bronchitis, Peptic ulcer, gastric carcinoma, gastric B-cell lymphoma, Legionnaire's Disease, Pontiac fever, Leptospirosis, Listeriosis, Leprosy (Hansen's disease), Tuberculosis, Mycoplasma pneumonia, Gonorrhea, Ophthalmia neonatorum, Septic arthritis, Meningococcal disease, Waterhouse-Friderichsen syndrome, Pseudomonas infection, Bacteremia, endocarditis, Rocky mountain spotted fever, Typhoid fever type salmonellosis (dysentery, colitis), Salmonellosis, gastroenteritis, enterocolitis, Bacillary dysentery/Shigellosis, Coagulase-positive staphylococcal infections: Impetigo, Acute infective endocarditis, Septicemia, Necrotizing pneumonia, Toxinoses, Toxic shock syndrome, Staphylococcal food poisoning, Cystitis, Meningitis, septicemia, Endometritis, Opportunistic infections, Acute bacterial pneumonia, Otitis media, sinusitis, Streptococcal pharyngitis, Scarlet fever, Rheumatic fever, erysipelas, Puerperal fever, Necrotizing fasciitis, Syphilis, Congenital syphilis, Cholera, Plague, Bubonic plague, Pneumonic plague, Iraq war infection caused by Acinetobacter baumannii (i.e., Iraq war-related Acinetobacter baumannii infection), necrotizing fasciitis, tuberculosis, hospital-acquired pneumonia, gastroenteritis, nosocomial infection, bacteremia, or sepsis. In some embodiments of the method of treating a disease, the disease is a nosocomial infection. In some embodiments of the method of treating a disease, the disease is ventilator associated pneumonia. In some embodiments of the method of treating a disease, the disease is bacteremia.

In some embodiments of the method of treating a disease, a compound as described herein (e.g., Formula (I), (II), (III), (IV), or (V)), is co-administered with an antibiotic. In some embodiments, the antibiotic is a β-lactam containing antibiotic. In some embodiments, the antibiotic is a cephalosporin. In some embodiments, the cephalosporin is a first generation cephalosporin. In some embodiments, the cephalosporin is a second generation cephalosporin. In some embodiments, the cephalosporin is a third generation cephalosporin. In some embodiments, the cephalosporin is a fourth generation cephalosporin. In some embodiments, the cephalosporin is a fifth generation cephalosporin. In some embodiments, the cephalosporin is a sixth generation cephalosporin. In some embodiments, the antibiotic is a penicillin. In some embodiments, the antibiotic is a carbapenem.

In a fifth aspect, a method of inhibiting the growth of a bacterium in a patient is provided, the method includes administering a therapeutically effective amount of a compound as described herein (e.g., Formula (I), (II), (III), (IV), or (V)). In some embodiments of the method of inhibiting the growth of a bacterium in a patient, the bacterium is killed. In some embodiments of the method of inhibiting the growth of a bacterium in a patient, replication of the bacterium is slowed. In some embodiments of the method of inhibiting the growth of a bacterium in a patient, the bacterium is a gram negative bacterium. In some embodiments of the method of inhibiting the growth of a bacterium in a patient, the bacterium is a gram positive bacterium. In some embodiments of the method of inhibiting the growth of a bacterium in a patient, the method includes administering a therapeutically effective amount of a compound as described herein (e.g., Formula (I), (II), (III), (IV), or (V)).

In further embodiments of the method of inhibiting the growth of a bacterium in a patient, the genera of the bacterium is selected from Stenotrophomonas, Clostridium, Acinetobacter, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio, Klebsiella, Enterobacter, Citrobacter, or Yersinia. In further embodiments of the method of inhibiting the growth of a bacterium in a patient, the bacteria is selected from Stenotrophomonas maltophilia, Clostridium difficile, Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Enterotoxigenic Escherichia coli (ETEC), Enteropathogenic E. coli, E. coli O157:H7, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Klebsiella pneumoniae, Enterobacter cloacae, Citrobacter freundii, Acinetobacter baumannii, or Yersinia pestis. In further embodiments of the method of inhibiting the growth of a bacterium in a patient, the bacteria is selected from a β-lactam antibiotic resistant strain of *Stenotrophomonas maltophilia, Clostridium difficile, Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli*, Enterotoxigenic *Escherichia coli* (ETEC), Enteropathogenic *E. coli, E. coli* O157:H7, *Francisella tularensis, Haemophilus influenzae, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Klebsiella pneumoniae, Enterobacter cloacae, Citrobacter freundii, Acinetobacter baumannii*, or *Yersinia pestis*.

In other embodiments, a method of inhibiting the hydrolysis of a β-lactam antibiotic by a bacterially expressed β-lactamase in a patient is provided. The method includes administering an effective amount of a compound as described herein (e.g., Formula (I), (II), (III), (IV), or (V)). In some embodiments of the method of inhibiting the hydrolysis of a β-lactam antibiotic by a bacterially expressed β-lactamase in a patient, the bacterium is a gram negative bacterium. In some embodiments of the method of inhibiting the hydrolysis of a β-lactam antibiotic by a bacterially expressed β-lactamase in a patient, the bacterium is a gram positive bacterium. In some embodiments of the method of inhibiting the hydrolysis of a β-lactam antibiotic by a bacterially expressed β-lactamase in a patient, the method includes administering an effective amount of a compound as described herein ((e.g., Formula (I), (II), (III), (IV), or (V)).

In further embodiments of the method of inhibiting the hydrolysis of a β-lactam antibiotic by a bacterially expressed β-lactamase in a patient, the genera of the bacterium is selected from *Stenotrophomonas, Clostridium, Acinetobacter, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio, Klebsiella, Enterobacter, Citrobacter*, or *Yersinia*. In further embodiments of the method of inhibiting the hydrolysis of a β-lactam antibiotic by a bacterially expressed β-lactamase in a patient, the bacteria is selected from *Stenotrophomonas maltophilia, Clostridium difficile, Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli*, Enterotoxigenic *Escherichia coli* (ETEC), Enteropathogenic *E. coli, E. coli* O157:H7, *Francisella tularensis, Haemophilus influenzae, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Klebsiella pneumoniae, Enterobacter cloacae, Citrobacter freundii, Acinetobacter baumannii*, or *Yersinia pestis*. In further embodiments of the method of inhibiting the hydrolysis of a β-lactam antibiotic by a bacterially expressed β-lactamase in a patient, the bacteria is selected from a β-lactam antibiotic resistant strain of *Stenotrophomonas maltophilia, Clostridium difficile, Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli*, Enterotoxigenic *Escherichia coli* (ETEC), Enteropathogenic *E. coli, E. coli* O157:H7, *Francisella tularensis, Haemophilus influenzae, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Klebsiella pneumoniae, Enterobacter cloacae, Citrobacter freundii, Acinetobacter baumannii*, or *Yersinia pestis*. In some embodiments of the method of inhibiting the hydrolysis of a β-lactam antibiotic by a bacterially expressed β-lactamase in a patient, the β-lactamase is a Class A β-lactamase. In some embodiments of the method of inhibiting the hydrolysis of a β-lactam antibiotic by a bacterially expressed β-lactamase in a patient, the β-lactamase is a Class B β-lactamase. In some embodiments of the method of inhibiting the hydrolysis of a β-lactam antibiotic by a bacterially expressed β-lactamase in a patient, the β-lactamase is a Class C β-lactamase. In some embodiments of the method of inhibiting the hydrolysis of a β-lactam antibiotic by a bacterially expressed β-lactamase in a patient, the β-lactamase is a Class D β-lactamase.

In further embodiments, a method of reducing the therapeutically effective amount of an antibiotic necessary to treat a patient in need of such treatment is provided, the method includes administering an effective amount of a compound as described herein (e.g., Formula (I), (II), (III), (IV), or (V)). In some embodiments, the antibiotic is a penicillin. In some embodiments, the antibiotic is a cephalosporin. In some embodiments, the antibiotic is a cephamycin. In some embodiments, the antibiotic is a first-generation cephalosporin. In some embodiments, the antibiotic is a second-generation cephalosporin. In some embodiments, the antibiotic is a third-generation cephalosporin. In some embodiments, the antibiotic is a fourth-generation cephalosporin. In some embodiments, the antibiotic is a fifth-generation cephalosporin. In some embodiments, the antibiotic is a sixth-generation cephalosporin. In some embodiments of the method of reducing the therapeutically effective amount of an antibiotic necessary to treat a patient in need of such treatment, the method includes administering an effective amount of a compound as described herein (e.g., Formula (I), (II), (III), (IV), or (V)).

In some embodiments of a method of reducing the therapeutically effective amount of an antibiotic necessary to treat a patient in need of such treatment, the antibiotic is selected from Cefacetrile (cephacetrile), Cefadroxil (cefadroxyl; Duricef), Cephalexin (cephalexin; Keflex), Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole, Cefaclor (Ceclor, Distaclor, Keflor, Raniclor), Cefonicid (Monocid), Cefprozil (cefproxil; Cefzil), Cefuroxime (Zefu, Zinnat, Zinacef, Ceftin, Biofuroksym, Xorimax), Cefuzonam, Cefmetazole, Cefotetan, Cefoxitin, Carbacephems, loracarbef (Lorabid); Cephamycins: cefbuperazone, cefmetazole (Zefazone), cefminox, cefotetan (Cefotan), cefoxitin (Mefoxin), Cefcapene, Cefdaloxime, Cefdinir (Zinir, Omnicef, Kefnir), Cefditoren, Cefetamet, Cefixime (Zifi, Suprax), Cefmenoxime, Cefodizime, Cefotaxime (Claforan), Cefovecin (Convenia), Cefpimizole, Cefpodoxime (Vantin, PECEF), Cefteram, Ceftibuten (Cedax), Ceftiofur, Ceftiolene, Ceftizoxime (Cefizox), Ceftriaxone (Rocephin), Cefoperazone (Cefobid), Ceftazidime (Fortum, Fortaz), Oxacephems: latamoxef (moxalactam), Cefclidine, Cefepime (Maxipime), Cefluprenam, Cefoselis, Cefozopran, Cefpirome (Cefrom), Cefquinome, Oxacephems, flomoxef, Ceftobiprole, Ceftaroline, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, or Cefuracetime.

In some embodiments of a method of treating a disease in a patient, reducing the therapeutically effective amount of an antibiotic necessary to treat a patient in need of such treatment, inhibiting the hydrolysis of a β-lactam antibiotic by a bacterially expressed β-lactamase in a patient, or inhibiting the growth of a bacterium in a patient, as described herein, the method further includes administering a β-lactam antibiotic to the patient. In some embodiments, the β-lactam antibiotic is a penicillin. In some embodiments, the β-lactam antibiotic is a cephalosporin. In some embodiments, the β-lactam antibiotic is a cephamycin. In some embodiments, the β-lactam antibiotic is a first-generation cephalosporin. In some embodiments, the β-lactam antibiotic is a second-generation cephalosporin. In some embodiments, the β-lactam antibiotic is a third-generation cephalosporin. In some embodiments, the β-lactam antibiotic is a fourth-generation cephalosporin. In some embodiments, the β-lactam antibiotic is a fifth-generation cephalosporin. In some embodiments, the β-lactam antibiotic is a sixth-generation cephalosporin. In some embodiments, the antibiotic is selected from Cefacetrile (cephacetrile), Cefadroxil (cefadroxyl; Duricef), Cephalexin (cephalexin; Keflex), Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole, Cefaclor (Ceclor, Distaclor, Keflor, Raniclor), Cefonicid (Monocid), Cefprozil (cefproxil; Cefzil), Cefuroxime (Zefu, Zinnat, Zinacef, Ceftin, Biofuroksym, Xorimax), Cefuzonam, Cefmetazole, Cefotetan, Cefoxitin, Carbacephems, loracarbef (Lorabid); Cephamycins: cefbuperazone, cefmetazole (Zefazone), cefminox, cefotetan (Cefotan), cefoxitin (Mefoxin), Cefcapene, Cefdaloxime, Cefdinir (Zinir, Omnicef, Kefnir), Cefditoren, Cefetamet, Cefixime (Zifi, Suprax), Cefmenoxime, Cefodizime, Cefotaxime (Claforan), Cefovecin (Convenia), Cefpimizole, Cefpodoxime (Vantin, PECEF), Cefteram, Ceftibuten (Cedax), Ceftiofur, Ceftiolene, Ceftizoxime (Cefizox), Ceftriaxone (Rocephin), Cefoperazone (Cefobid), Ceftazidime (Fortum, Fortaz), Oxacephems: latamoxef (moxalactam), Cefclidine, Cefepime (Maxipime), Cefluprenam, Cefoselis, Cefozopran, Cefpirome (Cefrom), Cefquinome, Oxacephems, flomoxef, Ceftobiprole, Ceftaroline, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, or Cefuracetime.

In further embodiments, a kit is provided for treating a bacterial infectious disease including a compound as described herein (e.g., Formula (I), (II), (III), (IV), or (V)) and a β-lactam containing antibiotic. In some embodiments of the kit for treating a bacterial infectious disease, the β-lactam containing antibiotic is a penicillin. In some embodiments of the kit for treating a bacterial infectious disease, the β-lactam containing antibiotic is a cephalosporin. In some embodiments, the β-lactam antibiotic is selected from Cefacetrile (cephacetrile), Cefadroxil (cefadroxyl; Duricef), Cephalexin (cephalexin; Keflex), Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole, Cefaclor (Ceclor, Distaclor, Keflor, Raniclor), Cefonicid (Monocid), Cefprozil (cefproxil; Cefzil), Cefuroxime (Zefu, Zinnat, Zinacef, Ceftin, Biofuroksym, Xorimax), Cefuzonam, Cefmetazole, Cefotetan, Cefoxitin, Carbacephems, loracarbef (Lorabid); Cephamycins: cefbuperazone, cefmetazole (Zefazone), cefminox, cefotetan (Cefotan), cefoxitin (Mefoxin), Cefcapene, Cefdaloxime, Cefdinir (Zinir, Omnicef, Kefnir), Cefditoren, Cefetamet, Cefixime (Zifi, Suprax), Cefmenoxime, Cefodizime, Cefotaxime (Claforan), Cefovecin (Convenia), Cefpimizole, Cefpodoxime (Vantin, PECEF), Cefteram, Ceftibuten (Cedax), Ceftiofur, Ceftiolene, Ceftizoxime (Cefizox), Ceftriaxone (Rocephin), Cefoperazone (Cefobid), Ceftazidime (Fortum, Fortaz), Oxacephems: latamoxef (moxalactam), Cefclidine, Cefepime (Maxipime), Cefluprenam, Cefoselis, Cefozopran, Cefpirome (Cefrom), Cefquinome, Oxacephems, flomoxef, Ceftobiprole, Ceftaroline. Additional cephems include Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, or Cefuracetime. In some embodiments of the kit for treating a bacterial infectious disease including a compound as described herein (e.g., Formula (I), (II), (III), (IV), or (V)) and a β-lactam containing antibiotic.

In other embodiments, a pharmaceutical composition is provided including a pharmaceutically acceptable excipient and a compound as described herein ((e.g., Formula (I), (II), (III), (IV), or (V)). In some embodiments, the pharmaceutical composition includes an antibiotic. In some embodiments, the antibiotic is a β-lactam containing antibiotic. In some embodiments, the antibiotic is a penicillin. In some embodiments, the antibiotic is a cephalosporin. In some embodiments, the antibiotic is a cephamycin. In some embodiments, the antibiotic is a first-generation cephalosporin. In some embodiments, the antibiotic is a second-generation cephalosporin. In some embodiments, the antibiotic is a third-generation cephalosporin. In some embodiments, the antibiotic is a fourth-generation cephalosporin. In some embodiments, the antibiotic is a fifth-generation cephalosporin. In some embodiments, the antibiotic is a sixth-generation cephalosporin. In some embodiments of the pharmaceutical composition including a pharmaceutically acceptable excipient and a compound as described herein (e.g., Formula (I), (II), (III), (IV), or (V)).

In some embodiments of a pharmaceutical composition, the antibiotic is selected from Cefacetrile (cephacetrile), Cefadroxil (cefadroxyl; Duricef), Cephalexin (cephalexin; Keflex), Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole, Cefaclor (Ceclor, Distaclor, Keflor, Raniclor), Cefonicid (Monocid), Cefprozil (cefproxil; Cefzil), Cefuroxime (Zefu, Zinnat, Zinacef, Ceftin, Biofuroksym, Xorimax), Cefuzonam, Cefmetazole, Cefotetan, Cefoxitin, Carbacephems, loracarbef (Lorabid); Cephamycins: cefbuperazone, cefmetazole (Zefazone), cefminox, cefotetan (Cefotan), cefoxitin (Mefoxin), Cefcapene, Cefdaloxime, Cefdinir (Zinir, Omnicef, Kefnir), Cefditoren, Cefetamet, Cefixime (Zifi, Suprax), Cefmenoxime, Cefodizime, Cefotaxime (Claforan), Cefovecin (Convenia), Cefpimizole, Cefpodoxime (Vantin, PECEF), Cefteram, Ceftibuten (Cedax), Ceftiofur, Ceftiolene, Ceftizoxime (Cefizox), Ceftriaxone (Rocephin), Cefoperazone (Cefobid), Ceftazidime (Fortum, Fortaz), Oxacephems: latamoxef (moxalactam), Cefclidine, Cefepime (Maxipime), Cefluprenam, Cefoselis, Cefozopran, Cefpirome (Cefrom), Cefquinome, Oxacephems, flomoxef, Ceftobiprole, Ceftaroline, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, or Cefuracetime.

The pharmaceutical compositions include optical isomers, diastereomers, or pharmaceutically acceptable salts of the modulators disclosed herein. The compound included in the pharmaceutical composition may be covalently attached to a carrier moiety, as described above. Alternatively, the compound included in the pharmaceutical composition is not covalently linked to a carrier moiety.

The compounds described herein can be administered alone or can be coadministered to the patient. Coadministration is meant to include simultaneous or sequential administration of the compounds individually or in combination (more than one compound). Thus, the preparations can also be combined, when desired, with other active substances (e.g., to reduce metabolic degradation).

The compounds described herein can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance, that may also act as diluents, flavoring agents, binders, preservatives, tablet disintegrating agents, or an encapsulating material.

In powders, the carrier is a finely divided solid in a mixture with the finely divided active component (e.g., a compound provided herein. In tablets, the active component is mixed with the carrier having the necessary binding properties in suitable proportions and compacted in the shape and size desired. The powders and tablets preferably contain from 5% to 70% of the active compound.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The compositions described herein may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Pharmaceutical compositions described herein may include compositions wherein the active ingredient is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. β-lactamase, class A β-lactamase, class B β-lactamase, class C β-lactamase, or class D β-lactamase), and/or reducing, eliminating, or slowing the progression of disease symptoms. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g., infectious disease, bacterial infectious disease, antibiotic resistant bacterial infectious disease), kind of concurrent treatment, complications from the disease being treated or other health-related problems. Other therapeutic regimens or agents can be used in conjunction with the methods and compounds of described herein. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. In one embodiment, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

The compositions described herein can be delivered transdermally, by a topical route, formulated as applicator sticks, solutions, suspensions, emulsions, gels, creams, ointments, pastes, jellies, paints, powders, and aerosols.

The compositions described herein can also be delivered as microspheres for slow release in the body. For example, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

The pharmaceutical compositions described herein can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the compositions described herein are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions described herein can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compounds described herein can be used in combination with one another, with other active agents known to be useful in treating an infectious disease (antibiotic, penicillin, cephalosporin, β-lactam containing antibiotic), or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents (compound as described herein and a β-lactam containing antibiotic). In other embodiments, the active agents can be formulated separately. In another embodiment, the active and/or adjunctive agents may be linked or conjugated to one another.

In some embodiments, the triazolylmethyl boronic acid β-lactamase inhibitors and optionally the antibiotic can be administered prior to a bacterial infection, after infection but prior to the manifestation of symptoms of a disease of disorder associated with the infection, or after the manifestation of symptoms associated with the production of one or more bacterial virulence factors to prevent further bacterial multiplication and to prevent further production of virulence factors thereby hindering development of the disease or its progression.

In another aspect, the triazolylmethyl boronic acid β-lactamase inhibitors and β-lactam antibiotics can be used to treat bacteria on or associated with a medical device by contacting the device with the triazolylmethyl boronic acid β-lactamase inhibitors and β-lactam antibiotics.

A medical device according to the application can comprise any instrument, implement, machine, contrivance, implant, or other similar or related article, including a component or part, or accessory which is: recognized in the official U.S. National Formulary the U.S. Pharmacopoeia, or any supplement thereof; intended for use in the diagnosis of disease or other conditions, or in the cure, mitigation, treatment, or prevention of disease, in humans or in other animals; or, intended to affect the structure or any function of the body of humans or other animals, and which does not achieve any of its primary intended purposes through chemical action within or on the body of human or other animal, and which is not dependent upon being metabolized for the achievement of any of its primary intended purposes.

A medical device can include, for example, endovascular medical devices, such as intracoronary medical devices. Examples of intracoronary medical devices can include stents, drug delivery catheters, grafts, and drug delivery balloons utilized in the vasculature of a subject. Where the medical device comprises a stent, the stent may include peripheral stents, peripheral coronary stents, degradable coronary stents, non-degradable coronary stents, self-expanding stents, balloon-expanded stents, and esophageal stents. The medical device may also include arterio-venous grafts, by-pass grafts, penile implants, vascular implants and grafts, intravenous catheters, small diameter grafts, artificial lung catheters, electrophysiology catheters, bone pins, suture anchors, blood pressure and stent graft catheters, breast implants, benign prostatic hyperplasia and prostate cancer implants, bone repair/augmentation devices, breast implants, orthopedic joint implants, dental implants, implanted drug infusion tubes, oncological implants, pain management implants, neurological catheters, central venous access catheters, catheter cuff, vascular access catheters, urological catheters/implants, atherectomy catheters, clot extraction catheters, PTA catheters, PTCA catheters, stylets (vascular and non-vascular), drug infusion catheters, angiographic catheters, hemodialysis catheters, neurovascular balloon catheters, thoracic cavity suction drainage catheters, electrophysiology catheters, stroke therapy catheters, abscess drainage catheters, biliary drainage products, dialysis catheters, central venous access catheters, and parental feeding catheters.

The medical device may additionally include either arterial or venous pacemakers, vascular grafts, sphincter devices, urethral devices, bladder devices, renal devices, gastroenteral and anastomotic devices, vertebral disks, hemostatic barriers, clamps, surgical staples/sutures/screws/plates/wires/clips, glucose sensors, blood oxygenator tubing, blood oxygenator membranes, blood bags, birth control/IUDs and associated pregnancy control devices, cartilage repair devices, orthopedic fracture repairs, tissue scaffolds, CSF shunts, dental fracture repair devices, intravitreal drug delivery devices, nerve regeneration conduits, electrostimulation leads, spinal/orthopedic repair devices, wound dressings, embolic protection filters, abdominal aortic aneurysm grafts and devices, neuroaneurysm treatment coils, hemodialysis devices, uterine bleeding patches, anastomotic closures, aneurysm exclusion devices, neuropatches, vena cava filters, urinary dilators, endoscopic surgical and wound drainings, bandages, surgical tissue extractors, transition sheaths and dialators, coronary and peripheral guidewires, circulatory support systems, tympanostomy vent tubes, cerebro-spinal fluid shunts, defibrillator leads, percutaneous closure devices, drainage tubes, bronchial tubes, vascular coils, vascular protection devices, vascular intervention devices including vascular filters and distal support devices and emboli filter/entrapment aids, AV access grafts, surgical tampons, and cardiac valves.

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

This Example describes the synthesis of enantiomerically-pure [(1,2,3-triazol-1-yl)methyl]boronic acids. This new scaffold can be obtained through CuAAC reaction between stereoisomerically pure 1-azidoalkylboronates and terminal acetylenes, catalyzed by copper sulfate, reduced in situ to CuI by sodium ascorbate in a tert-butanol/water system. Under these conditions, the proximity of the reaction center to the boronic group is not detrimental to the stability of the sp3 C—B bond to copper(I) catalysis, which further expands the functional group compatibility in CuAAC reaction beyond what is already known. Application of powerful click chemistry to boronates enables many analogs to be synthesized quickly.

Methods

All reactions were performed under an argon atmosphere with oven-dried glassware and dry solvents. Dry THF was obtained by standard methods and freshly distilled under an argon atmosphere from sodium benzophenone ketyl prior to use. All of the reagents were used as purchased from commercial suppliers without further purification. The −100° C. bath was prepared by addition of liquid nitrogen to a pre-cooled (−78° C.) mixture of 1:1 ethanol/methanol. Preloaded (0.25 mm) glass supported silica gel plates (Kieselgel 60, Merck) were used for TLC analysis, and compounds were visualized by exposure to UV light and by dipping the plates in $Ce(SO4).4H_2O$ (1%), $(NH_4)_6Mo_7O_{24}.4H_2O$ (2.5%) in sulfuric acid (10%) followed by heating on a hot plate. Melting points were measured in open capillary tubes with a Stuart SMP30 Melting Point apparatus. Optical rotations were determined at +20° C. with a Perkin-Elmer 241 polarimeter and are expressed in $10^{-1}$ degcm$_2$ g$^{-1}$. $^1H$ and $^{13}C$ NMR spectra were recorded with a Bruker Avance-400 MHz spectrometer. Chemical shifts were calibrated to the residual signals of the deuterated solvent. Multiplicity is given as s=singlet, d=doublet, t=triplet, q=quartet, m=multiplet, br.=broad signal. Two-dimensional NMR techniques (COSY, HMBC, HSQC) were used to aid in the assignment of signals in $^1H$ and $^{13}C$ spectra. In the 13C spectra the signal of the boron-bearing carbon atom tends to be broad, often below the detection limit; however, its resonance was always unambiguously determined by HSQC. The triazole ring carbon signals are often below the detection limit; when possible these were determined by HSQC and HMBC. High-resolution mass spectra were recorded with an Agilent Technologies 6520 Accurate-Mass Q-TOF LC/MS. Elemental analyses were performed with a Carlo Erba Elemental Analyzer 1110.

General Procedure for CuAAC Between Azidomethylboronates and Terminal Acetylenes Azidomethylboronate (1.00 mmol), the selected terminal alkyne (1.50 mmol), copper sulfate solution (50 mg/mL, 0.05 mmol) and sodium ascorbate (0.20 mmol) were dissolved in a mixture of tert-butanol and water (1:1; 2.0 mL of each). The reaction was stirred at room temperature for 2-16 h (as specified in each case), until the azido boronate disappeared as monitored by TLC. The mixture was then partitioned between ethyl acetate (20 mL), water (10 mL) and saturated NaCl (8 mL), and the aqueous phase extracted with ethyl acetate (2×20 mL). The combined organic phases were washed with brine (15 mL), dried with $Na_2SO_4$, filtered, and concentrated in vacuo, to afford the expected [(1,2,3-triazol-1-yl)methyl]boronate.

(+)-Pinanediyl [(4-Ethoxycarbonyl-1,2,3-triazol-1-yl) methyl]boronate (3a)

Yellow viscous oil (reaction time 2 h, 97%)

$[\alpha]_D^{20} = +13.6$ ($c = 1.3$, CHCl$_3$).

$^1H$ NMR (400 MHz, CDCl$_3$): δ=0.76 (s, 3 H, pinanyl CH$_3$), 1.03 (d, J=11.1 Hz, 1 H, pinanyl H$_{endo}$), 1.21 (s, 3 H, pinanyl CH$_3$), 1.32 (t, J=7.0 Hz, 3 H, OCH$_2$CH$_3$), 1.35 (s, 3 H, pinanyl CH$_3$), 1.77-2.30 (m, 5 H, pinanyl protons), 4.20 (s, 2 H, CH$_2$B), 4.29-4.35 (m, 3 H, CHOB, OCH$_2$CH$_3$), 8.19 (s, 1 H, CH$_{triaz}$) ppm. $^{13}C$ NMR (100 MHz, CDCl$_3$): δ=14.2, 23.8, 26.4, 26.9, 28.3, 34.9, 35.9 (br., CB), 38.1, 39.2, 51.0, 61.0, 78.9, 87.7, 128.6, 139.9, 160.9 ppm. HRMS (ESI-TOF) m/z: calcd. for C$_{16}$H$_{25}$BN$_3$O$_4$ [M+H]$^+$ 334.1936; found 334.1938.

(+)-Pinanediyl [(4-Carboxy-1,2,3-triazol-1-yl)methyl]boronate (3b)

White solid (reaction time 2 h, 85%), m.p. 110-113° C. dec $[\alpha]_D^{20} = +16.6$ ($c = 1.3$, CHCl$_3$).

$^1H$ NMR (400 MHz, CDCl$^3$): δ=0.82 (s, 3 H, pinanyl CH$_3$), 1.08 (d, J=11.1 Hz, 1 H, pinanyl H$_{endo}$), 1.27 (s, 3 H, pinanyl CH$_3$), 1.42 (s, 3 H, pinanyl CH$_3$), 1.84-2.37 (m, 5 H, pinanyl protons), 4.29 (s, 2 H, CH$_2$B), 4.39 (dd, J=8.7, 4.4 Hz, 1 H, CHOB), 8.37 (s, 1 H, CH$_{triaz}$), 9.57 (s, 1 H, COOH) ppm. $^{13}C$ NMR (100 MHz, CDCl$_3$): δ =24.1, 26.6, 27.1, 28.5, 35.1, 36.3 (br., CB), 38.3, 39.4, 51.1, 79.2, 88.0, 129.5, 139.3, 164.1 ppm. HRMS (ESI-TOF) m/z: calcd. for C$_{14}$H$_{21}$BN$_3$O$_4$ [M+H]$^+$ 306.1622; found 306.1624.

(+)-Pinanediyl [(4-Phenyl-1,2,3-triazol-1-yl)methyl]boronate (3c)

Yellow viscous oil (reaction time 16 h, 99%).

$[\alpha]_D^{20} = +13.0$ ($c = 2.2$, CHCl$_3$).

$^1H$ NMR (400 MHz, CDCl$_3$): δ=0.83 (s, 3 H, pinanyl CH$_3$), 1.15 (d, J=11.1 Hz, 1 H, pinanyl H$_{endo}$), 1.28 (s, 3 H, pinanyl CH$_3$), 1.43 (s, 3 H, pinanyl CH$_3$), 1.85-2.37 (m, 5 H, pinanyl protons), 4.24 (s, 2 H, CH$_2$B), 4.39 (dd, J=8.7, 1.8 Hz, 1 H, CHOB), 7.29 (t, J=7.4 Hz, 1 H, H$_{arom}$), 7.39 (t, J=7.9 Hz, 2 H, H$_{arom}$), 7.82 (d, J=7.4 Hz, 2 H, H$_{arom}$), 7.89 (s, 1 H, CH$_{triaz}$) ppm. $^{13}C$ NMR (100 MHz, CDCl$_3$): δ=24.0, 26.5, 27.0, 28.5, 35.1, 35.6 (br., CB), 38.2, 39.4, 51.1, 78.9, 87.5, 121.0, 125.7, 127.9, 128.8, 131.0, 147.6 ppm. HRMS (ESI-TOF) m/z: calcd. for C$_{19}$H$_{25}$BN$_3$O$_2$ [M+H]$^+$ 338.2038; found 338.2031.

(+)-Pinanediyl [(4-Thiophen-3-yl-1,2,3-triazol-1-yl)methyl] boronate (3d)

Yellow viscous oil (reaction time 16 h, 92%).

$[\alpha]_D^{20} = +10.2$ ($c = 0.9$, CHCl$_3$).

$^1H$ NMR (400 MHz, CDCl$_3$): δ=0.83 (s, 3 H, pinanyl CH$_3$), 1.14 (d, J=11.1 Hz, 1 H, pinanyl H$_{endo}$), 1.28 (s, 3 H, pinanyl CH$_3$), 1.43 (s, 3 H, pinanyl CH$_3$), 1.85-2.37 (m, 5 H, pinanyl protons), 4.23 (s, 2 H, CH$_2$B), 4.38 (dd, J=8.8, 1.7 Hz, 1 H, CHOB), 7.34 (dd, J=5.0, 2.9 Hz, 1H, CHCHS), 7.45 (dd, J=5.0, 1.1 Hz, 1 H, CHCHS), 7.64 (dd, J=2.9, 1.1 Hz, 1 H, CCHS), 7.79 (s, 1 H, CH$_{triaz}$) ppm. $^{13}C$ NMR (100 MHz, CDCl$_3$): δ=24.0, 26.6, 27.0, 28.5, 35.1, 35.8 (br., CB), 38.2, 39.4, 51.1, 78.9, 87.6, 120.8, 120.9, 126.0, 126.1, 132.3, 143.8 ppm. HRMS (ESITOF) m/z: calcd. for C$_{17}$H$_{23}$BN$_3$O$_2$S [M+H]$^+$ 344.1602; found 344.1610.

(+)-Pinanediyl [(4-Phenoxymethyl-1,2,3-triazol-1-yl) methyl]boronate (3e)

Yellow viscous oil (reaction time 8 h, 97%).

$[\alpha]_D^{20} = +13.1$ ($c = 2.1$, CHCl$_3$).

¹H NMR (400 MHz, CDCl₃): δ=0.85 (s, 3 H, pinanyl CH₃), 1.13 (d, J=11.1 Hz, 1 H, pinanyl $H_{endo}$), 1.30 (s, 3 H, pinanyl CH₃), 1.43 (s, 3 H, pinanyl CH₃), 1.85-2.39 (m, 5 H, pinanyl protons), 4.22 (s, 2 H, CH₂B), 4.39 (dd, J=8.8, 1.8 Hz, 1 H, CHOB), 5.21 (s, 2 H, OCH2), 6.96 (t, J=7.3 Hz, 1 H, $H_{arom}$), 7.00 (d, J=8.7 Hz, 2 H, $H_{arom}$), 7.28 (dd, J=8.7, 7.3 Hz, 2 H, $H_{arom}$), 7.77 (s, 1 H, $CH_{triaz}$) ppm. ¹³C NMR (100 MHz, CDCl₃): δ=24.0, 26.5, 27.0, 28.5, 35.1, 35.8 (br., CB), 38.2, 39.4, 51.1, 62.1, 78.9, 87.5, 114.9, 121.2, 124.1, 129.5, 143.9, 158.4 ppm. HRMS (ESI-TOF) m/z: calcd. for C₂₀H₂₇BN₃O₃ [M+H]+ 368.2144; found 368.2139.

General Procedure for Deprotection of Pinanediyl Boronates Through Transesterification To a solution of [(1,2,3-triazol-1-yl)-methyl]boronate (0.50 mmol) in CH3CN (3 mL), HCl (3 m aqueous solution, 1.50 mmol), phenylboronic acid (0.47 mmol), and n-hexane (3 mL) were sequentially added and the resulting biphasic solution was vigorously stirred. After 30 min the n-hexane layer, which contained the pinanediol phenylboronate, was removed and fresh n-hexane (3 mL) was added. This last step was repeated several times until a TLC analysis of the n-hexane layer revealed no phenylboronate production (total reaction time 3 h). The acetonitrile phase was then concentrated and the crude product was recrystallized from acetonitrile to afford [(1,2,3-triazol-1-yl)methyl]-boronic acid.

The enantiomeric purity of chiral boronic acids was checked by reconversion into their pinanediol esters. Final compounds 9a-9e, 18a-18e, and 19a-19e were allowed to react with an equimolar amount of (+)-pinanediol in anhydrous THF: the NMR spectra of the crude products displayed the presence of a single diastereoisomer, which proves that no epimerization occurred during the transesterification reaction.

[(4-Ethoxycarbonyl-1,2,3-triazol-1-yl)methyl]boronic Acid (4a)

White solid (80%), m.p. 123-125° C. dec. ¹H NMR (400 MHz, CD₃OD): δ=1.38 (t, J=7.1 Hz, 3 H, OCH₂CH₃), 4.27 (s, 2 H, CH₂B), 4.38 (q, J=7.1 Hz, 2 H, OCH₂CH₃), 8.38 (s, 1 H, $CH_{triaz}$) ppm. ¹³C NMR (100 MHz, CD₃OD): δ=14.6, 39.3 (br., CB), 62.1, 130.5, 140.4 ppm, COOEt not seen. HRMS (ESI-TOF) m/z: calcd. for C₆H₁₁BN₃O₄ [M+H]+ 200.0838; found 200.0840.

[(4-Carboxy-1,2,3-triazol-1-yl)methyl]boronic Acid (4b)

White solid (80%), m.p. 236-240° C. dec. ¹H NMR (400 MHz, CD₃OD): δ=4.26 (s, 2 H, CH₂B), 8.39 (s, 1 H, CHtriaz) ppm. 13C NMR (100 MHz, CD3OD): δ=39.9 (br., CB), 130.7, 140.6, 163.3 ppm. HRMS (ESI-TOF) m/z: calcd. for C₄H₇BN₃O₄ [M+H]+ 172.0525; found 172.0518.

[(4-Phenyl-1,2,3-triazol-1-yl)methyl]boronic Acid (4c)

Grey solid (98%), m.p. 122-124° C. dec. ¹H NMR (400 MHz, CD3OD): δ=4.48 (s, 2 H, CH₂B), 7.56-7.60 (m, 3 H, Harom), 7.83 (dd, J=7.8, 1.7 Hz, 2 H, $H_{arom}$), 8.78 (s, 1 H, $CH_{triaz}$) ppm. ¹³C NMR (100 MHz, CD₃OD): δ=42.6 (br., CB), 126.0, 126.8, 127.6, 130.7, 131.9, 144.7 ppm. HRMS (ESI-TOF) m/z: calcd. for C₉H₁₁BN₃O₂ [M+H]+ 204.0941; found 204.0940.

[(4-Thiophen-3-yl-1,2,3-triazol-1-yl)methyl]boronic Acid (4d)

White solid (100%), m.p. 170-172° C. dec. ¹H NMR (400 MHz, CD₃OD): δ=4.47 (s, 2 H, CH₂B), 7.55 (dd, J=5.1, 1.1 Hz, 1 H, CHCHS), 7.69 (dd, J=5.1, 2.8 Hz, 1 H, CHCHS), 8.08 (dd, J=2.8, 1.1 Hz, 1 H, CCHS), 8.70 (s, 1 H, $CH_{triaz}$) ppm. ¹³C NMR (100 MHz, CD₃OD): δ=42.7 (br., CB), 126.4, 126.5, 126.6, 127.0, 129.6, 140.4 ppm. HRMS (ESI-TOF) m/z: calcd. for C₇H₉BN₃O₂S [M+H]⁺ 210.0504; found 210.0498.

[(4-Phenoxymethyl-1,2,3-triazol-1-yl)methyl]boronic Acid (4e)

White solid (100%), m.p. 128-131° C. dec. ¹H NMR (400 MHz, CD₃OD): δ=4.44 (s, 2 H, CH₂B), 5.33 (s, 2 H, OCH₂), 7.01 (t, J=7.4 Hz, 1 H, Harom), 7.05 (dd, J=8.7, 0.8 Hz, 2 H, $H_{arom}$), 7.32 (dd, J=8.7, 7.4 Hz, 2 H, $H_{arom}$), 8.48 (s, 1 H, $CH_{triaz}$) ppm. ¹³C NMR (100 MHz, CD₃OD): δ=42.5 (br., CB), 60.4, 116.0, 123.1, 129.0, 130.8, 141.5, 159.0 ppm. HRMS (ESI-TOF) m/z: calcd. for C₁₀H₁₃BN₃O₃ [M+H]+ 234.1046; found 234.1048.

(+)-Pinanediyl [(1R)-1-Azido-3-methylbutyl]boronate (7)

To a solution of 6 (800 mg, 2.81 mmol) in ethyl acetate (10 mL), sodium azide (1.83 g, 28.1 mmol), tetrabutylammonium hydrogensulfate (475 mg, 1.40 mmol), and water (24 mL) were added and the system was vigorously stirred at room temperature overnight. The mixture was then diluted with saturated ammonium chloride/water (1:1, 40 mL) and extracted twice with light petroleum (60 mL, 30 mL). The combined organic fractions were washed again with saturated ammonium chloride/water (1:1, 20 mL), dried with Na₂SO₄, and filtered. Removal of solvent in vacuo afforded 7 as a colorless oil (794 mg, 97% yield).

$$[\alpha]_D^{20} = -7.1 \ (c = 1.7, CH_2Cl_2).$$

¹H NMR (400 MHz, CDCl₃): δ=0.83 (s, 3 H, pinanyl CH₃), 0.92 [d, J=6.6 Hz, 3H, CH(CH₃)₂], 0.93 [d, J=6.6 Hz, 3 H, CH(CH₃)²], 1.09 (d, J=11.0 Hz, 1H, pinanyl $H_{endo}$), 1.28 (s, 3 H, pinanyl CH₃), 1.40 (s, 3 H, pinanyl CH₃), 1.45 (ddd, J=14.0, 8.5, 5.4 Hz, 1 H, BCHCH₂), 1.63 (ddd, J=14.0, 10.0, 5.4 Hz, 1 H, BCHCH₂), 1.76-1.83 [m, 1 H, CH(CH₃)₂], 1.85-2.37 (m, 5 H, pinanyl protons), 3.11 (dd, J=10.0, 5.4 Hz, 1 H, BCH), 4.34 (dd, J=8.8, 1.8 Hz, 1 H, CHOB) ppm. ¹³C NMR (100 MHz, CDCl₃): δ=21.7, 23.1, 24.0, 25.7, 26.6, 27.1, 28.6, 35.4, 38.2, 39.3, 39.5, 46.4 (br., CB), 51.2, 78.5, 86.9 ppm. C₁₅H₂₆BN₃O₂ (291.20): calcd. C, 61.87; H, 9.00; N, 14.43; found C, 61.66; H, 9.21; N, 14.29.

(+)-Pinanediyl [(1R)-1-(4-Ethoxycarbonyl-1,2,3-triazol-1-yl)-3-methylbutyl]boronate (8a)

According to the general procedure reported above, CuAAC reaction between azido boronate 7 and ethyl propiolate (reaction time 2 h) afforded 8a as a yellow viscous oil (reaction time 2 h, 89%).

$$[\alpha]_D^{20} = +25.0 \ (c = 0.9, CHCl3).$$

¹H NMR (400 MHz, CDCl₃): δ=0.80 (s, 3 H, pinanyl CH₃), 0.83 [d, J=6.6 Hz, 3 H, CH(CH₃)₂], 0.90 [d, J=6.5 Hz, 3 H, CH(CH₃)₂], 1.03 (d, J=11.1 Hz, 1 H, pinanyl $H_{endo}$), 1.25 (s, 3 H, pinanyl CH₃), 1.28-1.34 [m, 1 H, CH(CH₃)₂], 1.38 (s, 3 H, pinanyl CH₃), 1.38 (t, J=7.0 Hz, 3 H, OCH₂CH₃), 1.71-2.34 (m, 7 H, pinanyl protons, BCHCH₂), 4.32 (d, J=8.7 Hz, 1 H, CHOB), 4.39 (q, J=7.0 Hz, 2 H, OCH₂CH₃), 4.60 (dd, J=10.3, 5.5 Hz, 1 H, BCH), 8.16 (s, 1 H, $CH_{triaz}$) ppm. ¹³C NMR (100 MHz, CDCl₃): δ=14.4, 21.4, 22.8, 24.0, 25.0, 26.5, 27.0, 28.5, 35.2, 38.2, 39.4, 41.4, 47.1 (br., CB), 51.1, 61.2, 78.9, 87.6, 127.5, 140.1, 161.2 ppm. HRMS (ESITOF) m/z: calcd. for C₂₀H₃₃BN₃O₄ [M+H]⁺ 390.2562; found 390.2563.

(+)-Pinanediyl [(1R)-1-(4-Carboxy-1,2,3-triazol-1-yl)-3-methylbutyl]boronate (8b)

Yellow viscous oil (reaction time 2 h, 91%).

$[\alpha]_D^{20} = +19.5$ ($c = 1.4$, CHCl$_3$).

$^1$H NMR (400 MHz, CDCl$_3$): δ=0.82 (s, 3 H, pinanyl CH$_3$), 0.86 [d, J=6.4 Hz, 3 H, CH(CH$_3$)$_2$], 0.94 [d, J=6.3 Hz, 3 H, CH(CH$_3$)$_2$], 1.04 (d, J=11.1 Hz, 1 H, pinanyl H$_{endo}$), 1.28 (s, 3 H, pinanyl CH$_3$), 1.32-1.37 [m, 1 H, CH(CH$_3$)$_2$], 1.41 (s, 3 H, pinanyl CH$_3$), 1.83-2.37 (m, 7 H, pinanyl protons, BCHCH$_2$), 4.35 (dd, J=8.7, 1.5 Hz, 1 H, CHOB), 4.65 (dd, J=10.3, 5.5 Hz, 1 H, BCH), 8.33 (s, 1 H, CH$_{triaz}$), 8.74 (br., 1 H, COOH) ppm. $^{13}$C NMR (100 MHz, CDCl$_3$): δ=21.4, 22.9, 24.0, 25.1, 26.5, 27.1, 28.5, 35.2, 38.3, 39.4, 41.4, 47.7 (br., CB), 51.1, 79.0, 87.8, 128.3, 139.4, 164.0 ppm. HRMS (ESI-TOF) m/z: calcd. for C$_{18}$H$_{29}$BN$_3$O$_4$ [M+H]$^+$ 362.2249; found 362.2254.

(+)-Pinanediyl [(1R)-3-Methyl-1-(4-phenyl-1,2,3-triazol-1-yl)butyl]-boronate (8c)

Yellow viscous oil (reaction time 16 h, 81%).

$[\alpha]_D^{20} = +11.8$ ($c = 1.8$, CHCl$_3$).

$^1$H NMR (400 MHz, CDCl$_3$): δ=0.84 (s, 3 H, pinanyl CH$_3$), 0.88 [d, J=6.6 Hz, 3 H, CH(CH$_3$)$_2$], 0.97 [d, J=6.5 Hz, 3 H, CH(CH$_3$)$_2$], 1.13 (d, J=11.0 Hz, 1 H, pinanyl H$_{endo}$), 1.29 (s, 3 H, pinanyl CH$_3$), 1.33-1.41 [m, 1 H, CH(CH$_3$)$_2$], 1.42 (s, 3 H, pinanyl CH$_3$), 1.73-2.38 (m, 7 H, pinanyl protons, BCHCH$_2$), 4.37 (dd, J=8.7, 1.6 Hz, 1 H, CHOB), 4.60 (dd, J=10.5, 5.6 Hz, 1 H, BCH), 7.31 (t, J=7.5 Hz, 1 H, H$_{arom}$), 7.41 (t, J=7.5 Hz, 2 H, H$_{arom}$), 7.85 (d, J=7.5 Hz, 2 H, H$_{arom}$), 7.86 (s, 1 H, CH$_{triaz}$) ppm. $^{13}$C NMR (100 MHz, CDCl$_3$): δ=21.6, 23.0, 24.1, 25.2, 26.6, 27.1, 28.6, 35.3, 38.3, 39.5, 41.6, 46.5 (br., CB), 51.2, 78.9, 87.4, 119.7, 125.8, 128.0, 128.9, 131.2, 147.5 ppm. HRMS (ESI-TOF) m/z: calcd. for C$_{23}$H$_{33}$BN$_3$O$_2$ [M+H]$^+$ 394.2665; found 394.2671.

(+)-Pinanediyl [(1R)-3-Methyl-1-(4-thiophen-3-yl-1,2,3-triazol-1-yl)-butyl]boronate (8d)

Yellow viscous oil (reaction time 16 h, 85%).

$[\alpha]_D^{20} = +13.1$ ($c = 1.6$, CHCl$_3$).

$^1$H NMR (400 MHz, CDCl$_3$): δ=0.84 (s, 3 H, pinanyl CH$_3$), 0.87 [d, J=6.6 Hz, 3 H, CH(CH$_3$)$_2$], 0.96 [d, J=6.5 Hz, 3 H, CH(CH$_3$)$_2$], 1.12 (d, J=11.0 Hz, 1 H, pinanyl H$_{endo}$), 1.29 (s, 3 H, pinanyl CH$_3$), 1.33-1.38 [m, 1 H, CH(CH$_3$)$_2$], 1.42 (s, 3 H, pinanyl CH$_3$), 1.72-2.37 (m, 7 H, pinanyl protons, BCHCH$_2$), 4.36 (d, J=7.2 Hz, 1 H, CHOB), 4.58 (dd, J=10.5, 5.5 Hz, 1 H, BCH), 7.36 (dd, J=4.8, 2.8 Hz, 1 H, CHCHS), 7.48 (d, J=4.8 Hz, 1 H, CHCHS), 7.67 (d, J=2.8 Hz, 1 H, CCHS), 7.75 (s, 1 H, CH$_{triaz}$) ppm. $^{13}$C NMR (100 MHz, CDCl$_3$): δ=21.5, 23.0, 24.0, 25.1, 26.5, 27.1, 28.6, 35.3, 38.3, 39.5, 41.6, 46.6 (br., CB), 51.2, 78.8, 87.4, 119.5, 120.8, 126.0, 126.1, 132.4, 143.7 ppm. HRMS (ESI-TOF) m/z: calcd. for C$_{21}$H$_{31}$BN$_3$O$_2$S [M+H]$^+$ 400.2228; found 400.2225.

(+)-Pinanediyl [(1R)-3-Methyl-1-(4-phenoxymethyl-3-yl-1,2,3-triazol-1-yl)butyl]boronate (8e)

Yellow viscous oil (reaction time 8 h, 97%).

$[\alpha]_D^{20} = +17.0$ ($c = 1.3$, CHCl$_3$).

$^1$H NMR (400 MHz, CDCl$_3$): δ=0.83 (s, 3 H, pinanyl CH$_3$), 0.85 [d, J=6.6 Hz, 3 H, CH(CH$_3$)$_2$], 0.94 [d, J=6.5 Hz, 3 H, CH(CH$_3$)$_2$], 1.07 (d, J=11.0 Hz, 1 H, pinanyl H$_{endo}$), 1.28 (s, 3 H, pinanyl CH$_3$), 1.30-1.36 [m, 1 H, CH(CH$_3$)$_2$], 1.40 (s, 3 H, pinanyl CH$_3$), 1.70-2.36 (m, 7 H, pinanyl protons, BCHCH$_2$), 4.34 (dd, J=8.7, 1.8 Hz, 1 H, CHOB), 4.55 (dd, J=10.2, 5.8 Hz, 1 H, BCH), 5.21 (s, 2 H, OCH$_2$), 6.96 (t, J=7.4 Hz, 1 H, H$_{arom}$), 6.99 (d, J=7.9 Hz, 2 H, H$_{arom}$), 7.28 (t, J=7.6 Hz, 2 H, H$_{arom}$), 7.69 (s, 1 H, CH$_{triaz}$) ppm. $^{13}$C NMR (100 MHz, CDCl$_3$): δ=21.6, 22.9, 24.0, 25.1, 26.5, 27.1, 28.5, 35.2, 38.3, 39.4, 41.5, 46.8 (br., CB), 51.2, 62.4, 78.8, 87.4, 115.0, 121.2, 122.8, 129.5, 144.0, 158.5 ppm. HRMS (ESI-TOF) m/z: calcd. for C$_{24}$H$_{35}$BN$_3$O$_3$ [M+H]+ 424.2770; found 424.2788.

[(1R)-1-(4-Ethoxycarbonyl-1,2,3-triazol-1-yl)-3-methylbutyl]boronic Acid (9a)

Following the general procedure reported above, pinanediol removal from 8a by transesterification reaction afforded 9a as a white solid (76% yield), m.p. 115-117° C. dec.

$[\alpha]_D^{20} = +9.2$ ($c = 0.8$, CH$_3$OH).

$^1$H NMR (400 MHz, CD$_3$OD): δ=0.84 [d, J=6.5 Hz, 3 H, CH(CH$_3$)$_2$], 0.92 [d, J=6.4 Hz, 3 H, CH(CH$_3$)$_2$], 1.14-1.24 [m, 1 H, CH(CH$_3$)$_2$], 1.37 (t, J=6.8 Hz, 3 H, OCH$_2$CH$_3$), 1.70-1.76 (m, 1 H, BCHCH$_2$), 1.90-1.97 (m, 1 H, BCHCH$_2$), 4.38 (q, J=6.8 Hz, 2 H, OCH$_2$CH$_3$), 4.53 (dd, J=10.8, 3.8 Hz, 1 H, BCH), 8.54 (s, 1 H, CH$_{triaz}$) ppm. $^{13}$C NMR (100 MHz, CD3OD): δ=14.5, 21.4, 23.3, 26.2, 41.7, 51.3 (br., CB), 62.1, 129.4, 140.5, 162.2 ppm. HRMS (ESI-TOF) m/z: calcd. for C$_{10}$H$_{19}$BN$_3$O$_4$ [M+H]+ 256.1465; found 256.1468.

[(1R)-1-(4-Carboxy-1,2,3-triazol-1-yl)-3-methylbutyl]boronic Acid (9b)

White solid (95%), m.p. 123-127° C. dec.

$[\alpha]_D^{20} = +4.5$ ($c = 0.4$, CH$_3$OH).

$^1$H NMR (400 MHz, CD$_3$OD): δ=0.86 [d, J=6.6 Hz, 3 H, CH(CH$_3$)$_2$], 0.94 [d, J=6.5 Hz, 3 H, CH(CH$_3$)$_2$], 1.20-1.27 [m, 1 H, CH(CH$_3$)$_2$], 1.72 (ddd, J=14.3, 8.9, 4.5 Hz, 1 H, BCHCH$_2$), 1.94 (ddd, J=14.3, 11.2, 4.7 Hz, 1 H, BCHCH$_2$), 4.58 (dd, J=11.2, 4.5 Hz, 1 H, BCH), 8.51 (s, 1 H, CH$_{triaz}$) ppm. $^{13}$C NMR (100 MHz, CD3OD): δ=21.4, 23.3, 26.3, 41.7, 51.1 (br., Synthesis of [(1,2,3-Triazol-1-yl)methyl] boronic Acids CB), 129.8, 141.0, 163.1 ppm. HRMS (ESI-TOF) m/z: calcd. for C8H15BN3O4 [M+H]$^+$ 228.1152; found 228.1148.

[(1R)-3-Methyl-1-(4-phenyl-1,2,3-triazol-1-yl)butyl]boronic Acid (9c)

Cream-colored solid (80%), m.p. 127-132° C. dec.

$[\alpha]_D^{20} = +8.0$ ($c = 0.5$, CH$_3$OH).

$^1$H NMR (400 MHz, CD$_3$OD): δ=0.92 [d, J=6.6 Hz, 3 H, CH(CH$_3$)$_2$], 0.98 [d, J=6.5 Hz, 3 H, CH(CH$_3$)$_2$], 1.31-1.38 [m, 1 H, CH(CH$_3$)$_2$], 1.84 (ddd, J=14.6, 9.3, 4.1 Hz, 1 H, BCHCH$_2$), 2.14 (ddd, J=14.6, 11.5, 4.5 Hz, 1 H, BCHCH$_2$), 4.69 (dd, J=11.5, 4.1 Hz, 1 H, BCH), 7.51-7.58 (m, 3 H, H$_{arom}$), 7.86 (d, J=6.8 Hz, 2 H, H$_{arom}$), 8.94 (s, 1 H, CH$_{triaz}$) ppm. $^{13}$C NMR (100 MHz, CD$_3$OD): δ=21.3, 23.3, 26.3, 40.8, 54.6 (br., CB), 125.7, 126.1, 127.6, 130.7, 131.9, 145.0 ppm. HRMS (ESITOF) m/z: calcd. for $C_{13}H_{19}BN_3O_2$ [M+H]$^+$ 260.1567; found 260.1563.

[(1R)-3-Methyl-1-(4-thiophen-3-yl-1,2,3-triazol-1-yl)butyl] boronic Acid (9d)

Cream-colored solid (92%), m.p. 130-132° C. dec.

$$[\alpha]_D^{20} = +6.2 \ (c = 0.6, CH_3OH).$$

$^1$H NMR (400 MHz, CD$_3$OD): δ=0.91 [d, J=6.6 Hz, 3 H, CH(CH$_3$)$_2$], 0.98 [d, J=6.6 Hz, 3 H, CH(CH$_3$) 2], 1.26-1.38 [m, 1 H, CH(CH$_3$)$_2$], 1.82 (ddd, J=14.6, 9.3, 4.3 Hz, 1 H, BCHCH$_2$), 2.10 (ddd, J=14.6, 11.5, 4.6 Hz, 1 H, BCHCH$_2$), 4.66 (dd, J=11.5, 4.3 Hz, 1 H, BCH), 7.56 (d, J=4.9 Hz, 1 H, CHCHS), 7.66 (dd, J=5.1, 2.8 Hz, 1 H, CHCHS), 8.04 (d, J=2.0 Hz, 1 H, CCHS), 8.78 (s, 1 H, CH$_{triaz}$) ppm. $^{13}$C NMR (100 MHz, CD$_3$OD): δ=21.3, 23.3, 26.3, 40.9, 54.3 (br., CB), 125.1, 126.3, 126.5, 127.3, 129.3, 141.3 ppm. HRMS (ESI-TOF) m/z: calcd. for $C_{11}H_{17}BN_3O_2S$ [M+H]$^+$ 266.1131; found 266.1137.

[(1R)-3-Methyl-1-(4-phenoxymethyl-3-yl-1,2,3-triazol-1-yl)butyl]-boronic Acid (9e)

White solid (77%), m.p. 118-123° C. dec.

$$[\alpha]_D^{20} = +2.9 \ (c = 1.2, CH_3OH).$$

$^1$H NMR (400 MHz, CD$_3$OD): δ=0.87 [d, J=6.6 Hz, 3 H, CH(CH$_3$)$_2$], 0.95 [d, J=6.5 Hz, 3 H, CH(CH$_3$)$_2$], 1.20-1.29 [m, 1 H, CH(CH$_3$)$_2$], 1.73 (ddd, J=14.5, 9.1, 4.5 Hz, 1 H, BCHCH$_2$), 1.97 (ddd, J=14.5, 11.3, 4.6 Hz, 1 H, BCHCH$_2$), 4.64 (dd, J=11.3, 4.5 Hz, 1 H, BCH), 5.24 (s, 2 H, OCH$_2$), 6.98 (tt, J=7.4, 1.0 Hz, 1 H, H$_{arom}$), 7.02 (d, J=8.7, 1.0 Hz, 2 H, H$_{arom}$), 7.30 (dd, J=8.7, 7.4 Hz, 2 H, H$_{arom}$), 8.30 (s, 1 H, CH$_{triaz}$) ppm. $^{13}$C NMR (100 MHz, CD3OD): —6=21.4, 23.3, 26.3, 41.4, 51.9 (br., CB), 61.4, 116.1, 122.7, 126.6, 130.6, 143.3, 159.3 ppm. HRMS (ESI-TOF) m/z: calcd. for $C_{14}H_{21}BN_3O_3$ [M+H]+ 290.1673; found 290.1673.

(+)-Pinanediyl [(1R)-1-Azido-2-phenylethyl]boronate (16)

Starting from 14[17] and following the procedure described for the synthesis of 7, compound 16 was recovered as a yellowish oil (94%).

$$[\alpha]_D^{20} = +8.7 \ (c = 1.0, CHCl_3).$$

$^1$H NMR (400 MHz, CDCl$_3$): δ=0.83 (s, 3 H, pinanyl CH$_3$), 0.98 (d, J=11.0 Hz, 1 H, pinanyl H$_{endo}$), 1.29 (s, 3 H, pinanyl CH$_3$), 1.38 (s, 3 H, pinanyl CH$_3$), 1.85-2.37 (m, 5 H, pinanyl protons), 2.95 (dd, J=14.0, 9.0 Hz, 1 H, BCHCH$_2$), 3.03 (dd, J=14.0, 5.7 Hz, 1 H, BCHCH$_2$), 3.38 (dd, J=9.0, 5.7 Hz, 1 H, BCH), 4.33 (dd, J=8.7, 1.7 Hz, 1 H, CHOB), 7.19-7.32 (m, 5 H, H$_{arom}$) ppm. $^{13}$C NMR (100 MHz, CDCl$_3$): δ=24.1, 26.5, 27.1, 28.6, 35.3, 36.9, 38.3, 39.5, 49.8 (br., CB), 51.2, 78.7, 87.1, 126.8, 128.6, 129.3, 138.8 ppm. $C_{18}H_{24}BN_3O_2$ (325.22): calcd. C, 66.48; H, 7.44; N, 12.92; found C, 66.25; H, 7.68; N, 12.72.

(+)-Pinanediyl [(1R)-1-Azido-2-(3-tert-butoxycarbonylphenyl)ethyl]-boronate (17)

Starting from 15[17] and following the procedure described for the synthesis of 7, compound 17 was recovered as a yellowish oil (97%).

$$[\alpha]_D^{20} = +11.9 \ (c = 1.8, CHCl_3).$$

$^1$H NMR (400 MHz, CDCl$_3$): δ=0.82 (s, 3 H, pinanyl CH$_3$), 0.93 (d, J=11.0 Hz, 1 H, pinanyl H$_{endo}$), 1.27 (s, 3 H, pinanyl CH$_3$), 1.37 (s, 3 H, pinanyl CH3), 1.59 (s, 9 H, tBu), 1.86-2.38 (m, 5 H, pinanyl protons), 2.99 (dd, J=13.9, 8.5 Hz, 1 H, BCHCH$_2$), 3.05 (dd, J=13.9, 6.0 Hz, 1 H, BCHCH$_2$), 3.39 (dd, J=8.5, 6.0 Hz, 1 H, BCH), 4.34 (d, J=7.6 Hz, 1 H, CHOB), 7.34 (t, J=7.7 Hz, 1 H, H$_{arom}$), 7.44 (d, J=7.7 Hz, 1 H, H$_{arom}$), 7.86 (d, J=7.7 Hz, 1 H, H$_{arom}$), 7.89 (s, 1 H, H$_{arom}$) ppm. $^{13}$C NMR (100 MHz, CDCl$_3$): δ=24.0, 26.4, 27.1, 28.3, 28.5, 35.2, 36.7, 38.2, 39.5, 49.5 (br., CB), 51.1, 78.7, 81.0, 87.1, 128.0, 128.4, 130.2, 132.3, 133.4, 138.8, 165.7 ppm. $C_{23}H_{32}BN_3O_4$ (425.33): calcd. C, 64.95; H, 7.58; N, 9.88; found C, 65.18; H, 7.81; N, 9.64.

[(1R)-1-(4-Ethoxycarbonyl-1,2,3-triazol-1-yl)-2-phenylethyl]boronic Acid (18a)

According to the general procedure reported above, CuAAC reaction between azido boronate 16 and ethyl propiolate (reaction time 2 h) followed by deprotection of pinanediol boronate ester through transesterification reaction afforded 18a as a white solid (75% overall yield), m.p. 147-149° C. dec.

$$[\alpha]_D^{20} = -53.7 \ (c = 1.1, CH_3OH).$$

$^1$H NMR (400 MHz, CD$_3$OD): δ=1.34 (t, J=7.1 Hz, 3 H, OCH$_2$CH$_3$), 3.20 (dd, J=14.0, 9.9 Hz, 1 H, BCHCH$_2$), 3.25-3.31 (m, 1 H, BCHCH$_2$ and CD$_3$OD), 4.33 (q, J=7.1 Hz, 2 H, OCH$_2$CH$_3$), 4.62 (dd, J=9.9, 4.9 Hz, 1 H, BCH), 6.97 (d, J=7.0 Hz, 2 H, H$_{arom}$), 7.14-7.20 (m, 3 H, H$_{arom}$), 8.16 (s, 1 H, CH$_{triaz}$) ppm. $^{13}$C NMR (100 MHz, CD$_3$OD): δ=14.5, 39.2, 55.4 (br., CB), 62.2, 127.7, 129.5, 129.7, 130.4, 139.3, 162.3 ppm, C-4 triazole ring not seen. HRMS (ESI-TOF) m/z: calcd. for $C_{13}H_{17}BN_3O_4$ [M+H]$^+$ 290.1309; found 290.1295.

[(1R)-1-(4-Carboxy-1,2,3-triazol-1-yl)-2-phenylethyl]boronic Acid (18b)

White solid (reaction time 2 h, 85% overall yield), m.p. 120-122° C. dec.

$$[\alpha]_D^{20} = -43.4 \ (c = 1.0, CH_3OH).$$

$^1$H NMR (400 MHz, CD$_3$OD): δ=3.18 (dd, J=14.0, 10.0 Hz, 1 H, BCHCH$_2$), 3.27-3.32 (m, 1 H, BCHCH$_2$ and CD$_3$OD), 4.68 (dd, J=10.0, 5.6 Hz, 1 H, BCH), 7.00 (d, J=6.6 Hz, 2 H, H$_{arom}$), 7.14-7.22 (m, 3 H, H$_{arom}$), 8.15 (s, 1 H, CH$_{triaz}$) ppm. $^{13}$C NMR (100 MHz, CD$_3$OD): δ=39.3, 54.5 (br., CB), 127.8, 129.5, 129.8, 130.3, 139.2, 140.4, 163.2 ppm. HRMS (ESI-TOF) m/z: calcd. for $C_{11}H_{13}BN_3O_4$ [M+H]$^+$ 262.0996; found 262.0994.

[(1R)-1-(4-Phenyl-1,2,3-triazol-1-yl)-2-phenylethyl]boronic Acid (18c)

White solid (reaction time 16 h, 70% overall yield), m.p. 151-153° C. dec.

$$[\alpha]_D^{20} = -62.3 \ (c = 1.3, CH_3OH).$$

¹H NMR (400 MHz, CD₃OD): δ=3.25-3.31 (m, 1 H, BCHCH₂ and CD₃OD), 3.39 (dd, J=14.1, 5.7 Hz, 1 H, BCHCH₂), 4.84 (dd, J=10.0, 5.7 Hz, 1 H, BCH), 7.12 (d, J=6.9 Hz, 2 H, H$_{arom}$), 7.16-7.25 (m, 3 H, H$_{arom}$), 7.44-7.52 (m, 3 H, H$_{arom}$), 7.73 (d, J=6.7 Hz, 2 H, H$_{arom}$), 8.51 (s, 1 H, CH$_{triaz}$) ppm. ¹³C NMR (100 MHz, CD₃OD): δ=38.8, 56.3 (br., CB), 125.1, 127.2, 127.8, 128.1, 129.7, 129.9, 130.4, 131.1, 138.8, 145.9 ppm. HRMS (ESI-TOF) m/z: calcd. for C₁₆H₁₇BN₃O₂ [M+H]+ 294.1411; found 294.1423.

[(1R)-2-Phenyl-1-(4-thiophen-3-yl-1,2,3-triazol-1-yl)ethyl]boronic Acid (18d)

Cream-colored solid (reaction time 16 h, 80% overall yield), m.p. 141-143° C. dec.

$[\alpha]_D^{20} = -67.3$ ($c = 1.1$, CH₃OH).

¹H NMR (400 MHz, CD₃OD): δ=3.25-3.32 (m, 1 H, BCHCH₂ and CD₃OD), 3.40 (dd, J=14.2, 5.7 Hz, 1 H, BCHCH₂), 4.87 (dd, J=10.6, 5.7 Hz, 1 H, BCH), 7.13 (d, J=6.9 Hz, 2 H, H$_{arom}$), 7.17-7.25 (m, 3 H, H$_{arom}$), 7.47 (d, J=5.0 Hz, 1 H, H$_{arom}$), 7.63 (dd, J=5.0, 2.8 Hz, 1 H, H$_{arom}$), 7.94 (d, J=1.9 Hz, 1 H, H$_{arom}$), 8.57 (s, 1 H, CH$_{triaz}$) ppm. ¹³C NMR (100 MHz, CD₃OD): δ=38.7, 56.7 (br., CB), 125.3, 126.0, 126.5, 127.5, 128.1, 129.2, 129.7, 129.8, 138.6, 141.5 ppm. HRMS (ESI-TOF) m/z: calcd. for C₁₄H₁₅BN₃O₂S [M+H]+ 300.0975; found 300.0987.

[(1R)-2-Phenyl-1-(4-phenoxymethyl-1,2,3-triazol-1-yl)ethyl]boronic Acid (18e)

White solid (reaction time 16 h, 79% overall yield), m.p. 113-115° C. dec.

$[\alpha]_D^{20} = -50.1$ ($c = 0.8$, CH₃OH).

¹H NMR (400 MHz, CD₃OD): δ=3.13 (dd, J=14.0, 9.8 Hz, 1 H, BCHCH₂), 3.24-3.32 (m, 1 H, BCHCH₂ and CD₃OD), 4.67 (dd, J=9.8, 5.8 Hz, 1 H, BCH), 5.10 (s, 2 H, OCH₂), 6.93-6.97 (m, 5 H, H$_{arom}$), 7.14-7.16 (m, 3 H, H$_{arom}$), 7.25-7.29 (m, 2 H, H$_{arom}$), 7.92 (s, 1 H, CH$_{triaz}$) ppm. ¹³C NMR (100 MHz, CD₃OD): δ=39.4, 53.9 (br., CB), 62.1, 116.0, 122.3, 127.7, 129.5, 129.76, 129.85, 130.5, 139.4, 159.6 ppm, C-4 triazole ring not seen. HRMS (ESITOF) m/z: calcd. for C₁₇H₁₉BN₃O₃ [M+H]+ 324.1517; found 324.1513.

[(1R)-1-(4-Carboxy-1,2,3-triazol-1-yl)-2-(3-carboxyphenyl)ethyl]-boronic Acid (19a)

According to the general procedure reported above, the product of the CuAAC reaction between azido boronate 17 and ethyl propiolate (reaction time 2 h) was firstly subjected to tert-butyl group removal (trifluoroacetic anhydride 25% v/v in CH₂Cl₂, 2 mL, room temp., 5 h) followed by deprotection of pinanediol boronate ester through transesterification reaction afforded 19a as a white solid (64% overall yield), m.p. 157-159° C. dec.

$[\alpha]_D^{20} = -54.9$ ($c = 1.2$, CH₃OH).

¹H NMR (400 MHz, CD₃OD): δ=1.35 (t, J=7.1 Hz, 3 H, OCH₂CH₃), 3.24 (dd, J=14.0, 10.0 Hz, 1 H, BCHCH₂), 3.34 (dd, J=14.0, 5.2 Hz, 1 H, BCHCH₂), 4.34 (q, J=7.1 Hz, 2 H, OCH₂CH₃), 4.75 (m, 1 H, BCH), 7.26 (d, J=7.6 Hz, 1 H, H$_{arom}$), 7.33 (t, J=7.6 Hz, 1 H, H$_{arom}$), 7.69 (s, 1 H, H$_{arom}$), 7.85 (d, J=7.6 Hz, 1 H, H$_{arom}$), 8.23 (s, 1 H, CH$_{triaz}$) ppm. ¹³C NMR (100 MHz, CD₃OD): δ=14.5, 39.1, 54.4 (br., CB), 62.1, 128.5, 129.2, 129.6, 130.3, 131.2, 134.5, 139.9, 162.1, 169.4 ppm, C-4 triazole ring not seen. HRMS (ESI-TOF) m/z: calcd. for C₁₄H₁₇BN₃O₆ [M+H]+ 334.1204; found 334.1208.

[(1R)-2-(3-Carboxyphenyl)-1-(4-ethoxycarbonyl-1,2,3-triazol-1-yl)-ethyl]boronic Acid (19b)

White solid (reaction time 2 h, 55% overall yield), m.p. 108-110° C. dec.

$[\alpha]_D^{20} = -49.2$ ($c = 1.5$, CH₃OH).

¹H NMR (400 MHz, CD₃OD): δ=3.26 (dd, J=14.0, 10.1 Hz, 1 H, BCHCH₂), 3.31-3.41 (m, 1 H, BCHCH₂ and CD₃OD), 4.71 (br., 1 H, BCH), 7.22 (d, J=7.7 Hz, 1 H, H$_{arom}$), 7.32 (t, J=7.7 Hz, 1 H, H$_{arom}$), 7.71 (s, 1 H, H$_{arom}$), 7.84 (d, J=7.7 Hz, 1 H, H$_{arom}$), 8.18 (s, 1 H, CH$_{triaz}$) ppm. ¹³C NMR (100 MHz, CD₃OD): δ=39.1, 53.9 (br., CB), 128.5, 129.2, 129.6, 131.2, 132.2, 134.6, 139.9, 140.8, 163.5, 169.6 ppm. HRMS (ESI-TOF) m/z: calcd. for C₁₂H₁₁BN₃O₆[M−H]− 304.0749; found 304.0739.

[(1R)-2-(3-Carboxyphenyl)-1-(4-phenyl-1,2,3-triazol-1-yl)ethyl]-boronic Acid (19c)

White solid (reaction time 16 h, 79% overall yield), m.p. 88-90° C. dec.

$[\alpha]_D^{20} = -70.0$ ($c = 1.0$, CH₃OH).

¹H NMR (400 MHz, CD₃OD): δ=3.26-3.32 (m, 1 H, BCHCH₂ and CD₃OD), 3.39 (dd, J=14.1, 5.8 Hz, 1 H, BCHCH₂), 4.74 (dd, J=9.9, 5.8 Hz, 1 H, BCH), 7.29-7.44 (m, 5 H, H$_{arom}$), 7.71 (d, J=7.4 Hz, 2 H, H$_{arom}$), 7.76 (s, 1 H, H$_{arom}$), 7.85 (d, J=7.2 Hz, 1H, H$_{arom}$), 8.17 (s, 1 H, CH$_{triaz}$) ppm. ¹³C NMR (100 MHz, CD₃OD): δ=39.1, 54.0 (br., CB), 123.6, 126.8, 129.2, 129.7, 130.00, 130.06, 131.2, 132.2, 134.7, 140.0, 147.1, 169.6 ppm, C-4 triazole ring not seen. HRMS (ESI-TOF) m/z: calcd. for C₁₇H₁₇BN₃O₄ [M+H]+ 338.1310; found 338.1310.

[(1R)-2-(3-Carboxyphenyl) 1-(4-thiophen-3-yl-1,2,3-triazol-1-yl)ethyl]boronic Acid (19d)

Cream-colored solid (reaction time 16 h, 60% overall yield), m.p. 185-187° C. dec.

$[\alpha]_D^{20} = -69.4$ ($c = 0.7$, CH₃OH).

¹H NMR (400 MHz, CD₃OD): δ=3.32 (dd, J=14.2, 10.2 Hz, 1 H, BCHCH₂), 3.41 (dd, J=14.2, 5.6 Hz, 1 H, BCHCH₂), 4.76 (dd, J=10.2, 5.6 Hz, 1 H, BCH), 7.30-7.44 (m, 3 H, H$_{arom}$), 7.54 (dd, J=5.0, 2.9 Hz, 1 H, H$_{arom}$), 7.75 (s, 1 H, H$_{arom}$), 7.79 (d, J=1.9 Hz, 1 H, H$_{arom}$), 7.84 (d, J=6.8 Hz, 1 H, H$_{arom}$), 8.28 (s, 1 H, CH$_{triaz}$) ppm. ¹³C NMR (100 MHz, CD₃OD): δ=38.8, 55.2 (br., CB), 124.1 (2C), 126.6, 128.3, 129.3, 129.7, 131.1, 132.2, 134.5, 134.6, 139.7, 142.9, 169.5 ppm. HRMS (ESI-TOF) m/z: calcd. for $C_{15}H_{15}BN_3O_4S$ [M+H]+ 344.0874; found 344.0873.

[(1R)-2-(3-Carboxyphenyl) 1-(4-phenoxymethyl-3-yl-1,2,3-triazol-1-yl)ethyl]boronic Acid (19e)

White solid (reaction time 8 h, 54% overall yield), m.p. 182-184° C. dec.

$[\alpha]_D^{20} = -37.1$ ($c = 1.3$, $CH_3OH$).

$^1$H NMR (400 MHz, $CD_3OD$): δ=3.21 (dd, J=14.1, 10.1 Hz, 1 H, $BCHCH_2$), 3.32 (dd, J=14.1, 5.6 Hz, 1 H, $BCHCH_2$), 4.72 (dd, J=10.1, 5.6 Hz, 1 H, BCH), 5.10 (s, 2 H, $OCH_2$), 6.92-6.96 (m, 3 H, $H_{arom}$), 7.17-7.28 (m, 4 H, $H_{arom}$), 7.71 (s, 1 H, $H_{arom}$), 7.82 (d, J=7.7 Hz, 1 H, $H_{arom}$), 7.89 (s, 1 H, $CH_{triaz}$) ppm. $^{13}$C NMR (100 MHz, $CD_3OD$): δ=39.2, 53.6 (br., CB), 62.1, 116.0, 122.3, 127.1, 129.1, 129.6, 130.5, 131.2, 132.1, 134.6, 139.9, 159.6, 169.6 ppm, C-4 triazole ring not seen. HRMS (ESI-TOF) m/z: calcd. for $C_{18}H_{19}BN_3O_5$ [M+H]+ 368.1416; found 368.1411.

Results and Calculations

Initial experiments focused on the synthesis of the simplest boronic ester, which corresponding to triazolyl analogs of acyl-boroGly (Scheme 1).

Scheme 1. Synthesis of triazolyl analog of acyl-boroGly 3a.

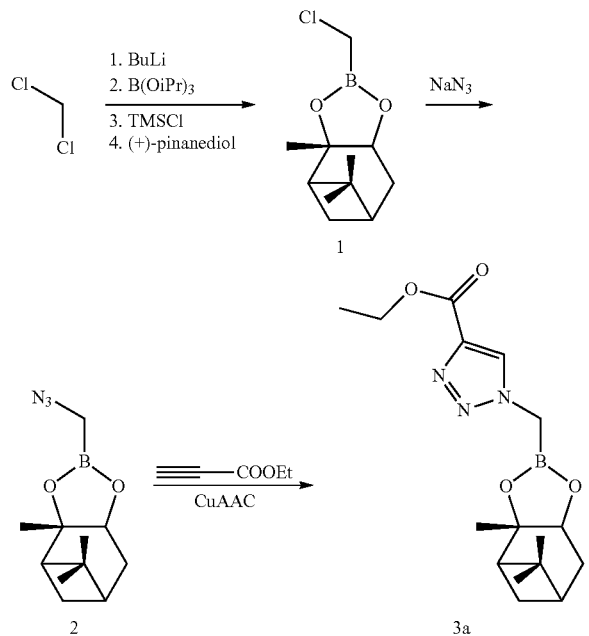

Tested conditions for the CuAAC reaction: a) CuI, DIPEA, THF; b) CuI, lutidine, CHCl3; c) $CuSO_4$, sodium ascorbate, tBuOH, $H_2O$; TMSCl = trimethylsilyl chloride.

By starting from pinanediyl (chloromethyl)boronate (1), substitution with sodium azide was catalyzed by tetrabutylammonium iodide, as a phase transfer agent, to yield the (azidomethyl)boronate 2 (97%). The use of (+)-pinanediol to esterify the boronic acid group is justified by its strong stability to hydrolysis, which allows the use of TLC as a reaction monitoring method. An investigation of CuAAC reaction feasibility on azido intermediate 2 was performed with ethyl propiolate as the acetylene counterpart, which was chosen because of the general observation that α-carbonyl groups are more reactive than alkyl- or aryl-alkynes.

From the wide variety of conditions described in the literature for CuAAC reactions, we selected three. In two cases the copper(I) catalyst was added directly in the presence of a ligand [CuI, N,N-diisopropylethylamine (DIPEA), tetrahydrofuran (THF), or CuI, lutidine, $CHCl_3$]. In the third case, the catalytically active metal was generated in situ by reduction of copper sulfate ($CuSO_4$, sodium ascorbate, tert-butanol, $H_2O$). Each experiment was performed at room temperature for 6 h with a molar ratio of 2/ethyl propiolate/catalyst 1:1.5:0.1. The crude product was analyzed by $^1$H NMR spectroscopy and LC-MS, and formation of expected and previously unreported product 3a in almost complete conversion was observed in all of the three experiments, which confirms the robustness of the CuAAC reaction. Nevertheless, when the CuI catalyst was adopted, the NMR spectra revealed the presence of proto-deboronation by-products (5-20%), and these were more pronounced when more basic DIPEA rather than lutidine was used as ligand. However DIPEA could be easily removed from the crude mixture under reduced pressure, whereas lutidine could not. Superior performance in terms of purity of the recovered material and absence of deboronation by-products was observed under aqueous conditions. Consequently these conditions were therefore applied to the cycloaddition reactions of 2 with several other alkynes. Among the many compounds commercially available, carbonyl, aromatic, and aliphatic alkynes were chosen. In the optimized procedure, azide 2 and an excess of alkyne (1.5 equiv.) were dissolved in a 1:1 mixture of tert-butanol and water, together with copper sulfate (0.05 equiv.), which was reduced in situ by sodium ascorbate (0.2 equiv.). The cyclization reactions were carried out at room temperature and monitored by TLC until no azidomethylboronate 2 remained. Complete conversion was reached in two hours with propiolic acid and ethyl propiolate (Table 1, Entries 1-2), whereas longer reaction times (up to 16 h) were required for alky- and aryl-alkynes (Table 1, Entries 3-5). The expected 1,4-disubstituted triazoles were easily isolated by extraction, and any residual alkyne was removed under reduced pressure, to afford 3a-3e in good to excellent yields (85-99%) with high purity. The cyclization product was confirmed by the presence of a singlet signal downfield in the aromatic region in the $^1$H NMR spectra and the expected 1,4-regioselectivity was supported by bidimensional spectroscopy [particularly the 3J(C,H) correlation between protons on the boron-bearing carbon atom and the unsubstituted carbon of the triazole ring]. Final deprotection of (+)-pinanediol was acSynthesis of [(1,2,3-Triazol-1-yl)methyl]boronic Acids complished by transesterification with phenylboronic acid in a biphasic system of acetonitrile/n-hexane, to give desired boronic acids 4a-4e, which were purified by crystallization from acetonitrile (80-100%).

TABLE 1

Copper-catalyzed azide-alkyne cycloaddition reaction between α-azidomethylboronate 2 and several alkynes

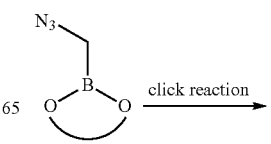

TABLE 1-continued

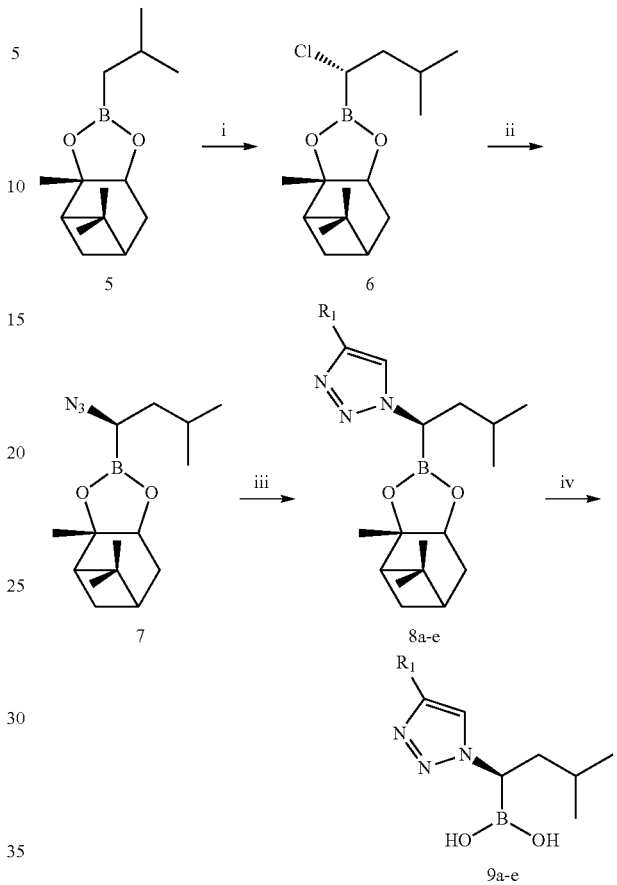

Scheme 2. Stereoselective synthesis of triazolyl analogs of acyl-boroLeu.

(i) LiCHCl₂, ZnCl₂, THF, −100° C. → room temp.; (ii) NaN₃, TBAHS, EtOAc, H₂O, room temp.; (iii) alkyne, CuSO₄, sodium ascorbate, tBuOH, H2O, room temp.; (iv) phenylboronic acid, HCl, acetonitrile, n-hexane, room temp.

| Entry | R₁ | Click reaction Product | Time (h) | Yield (%) | Deprotection Product | Yield (%) |
|---|---|---|---|---|---|---|
| 1 | ethyl ester | 3a | 2 | 97 | 4a | 80 |
| 2 | carboxylic acid | 3b | 2 | 85 | 4b | 80 |
| 3 | phenyl | 3c | 16 | 99 | 4c | 98 |
| 4 | thiophene | 3d | 16 | 92 | 4d | 100 |
| 5 | phenoxymethyl | 3e | 8 | 97 | 4e | 100 |

The successful synthesis of these [(1,2,3-triazol-1-yl)-methyl]boronic acids prompted us to expand our project toward chiral compounds and introduce a R2-substituent (see FIG. 1, b). To obtain a homochiral series with natural amino acids a stereoselective synthesis was required. At first we focused on triazolyl analogs of acyl-boroLeu that bear an isobutyl moiety as the R2 group (Scheme 2), a structure that is also part of Velcade® (A).

The configuration of the carbon in αposition to the boron is controlled through Matteson's homologation of boronic esters, when (+)-pinanediol is used as the chiral auxiliary agent. Following this procedure, isobutylboronate 5 was treated with dichloromethyllithium generated in situ at −100° C. for the insertion of a halogenated and asymmetrically substituted carbon on the C—B bond. According to the literature, the use of (+)-pinanediol in 6 induced the S absolute configuration with high diastereoselectivity (de>98%, yield 70%). Subsequent substitution with so-dium azide afforded azido boronate 7 (de>98%, yield 97%). With respect to the synthesis of 2, the presence of a stereogenic center at the reactive site prevents the use of tetrabutylammonium iodide (TBAI) in favor of non-nucleo-philic tetrabutylammonium hydrogensulfate (TBAHS) to avoid epimerization (30% of undesired epimer was obtained with TBAI). Click reactions to give 8a-8e under the same conditions described for the synthesis of 3a-3e performed equally well without any effect on reaction time (2-16 h, see the Experimental Section) or yield (81-97%). Most importantly, no effect on the diastereoisomeric composition was observed in the NMR spectra, which was evaluated through analyses of the spectra of 8a-8e obtained from an epimeric mixture of 7. Final deprotection afforded enantiomerically pure triazolyl boronic acids 9a-9e (Table 2, Entries 1-5).

TABLE 2

Copper-catalyzed azide-alkyne cycloaddition reaction between chiral α-azidomethylboronates and alkynes

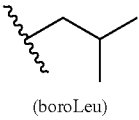

| Entry | Product | R₂ | R₁ | Overall yield (%) |
|---|---|---|---|---|
| 1 | 9a | 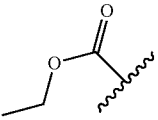 [SMILES: *C(=O)OCC] (boroLeu) | 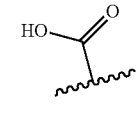 | 68 |
| 2 | 9b | | 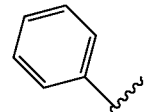 | 86 |
| 3 | 9c | | 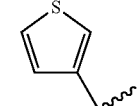 | 65 |
| 4 | 9d | | 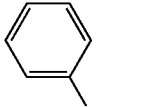 | 78 |
| 5 | 9e | | 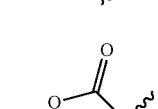 | 75 |
| 6 | 18a | 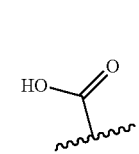 (boroPhe) |  | 75 |
| 7 | 18b | | 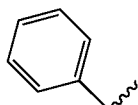 | 85 |
| 8 | 18c | | 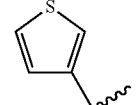 | 70 |
| 9 | 18d | | 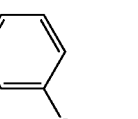 | 80 |
| 10 | 18e | | 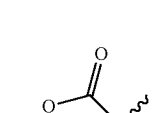 | 79 |
| 11 | 19a |  (boro-m-COOH-Phe) |  | 64 |
| 12 | 19b | | 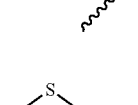 | 55 |
| 13 | 19c | |  | 79 |
| 14 | 19d | | 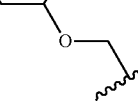 | 60 |
| 15 | 19e | | | 54 |

The same procedure was replicated for the synthesis of boroPhe analogs 18a-18e and 19a-19e (Scheme 3), which bear as the R2 group a benzyl or its meta-carboxy derivative; the latter of which is a recurring motif in β-lactamase inhibitors (FIG. 1, C).

Scheme 3. Stereoselective synthesis of triazolyl analogs of acylboroPhe.

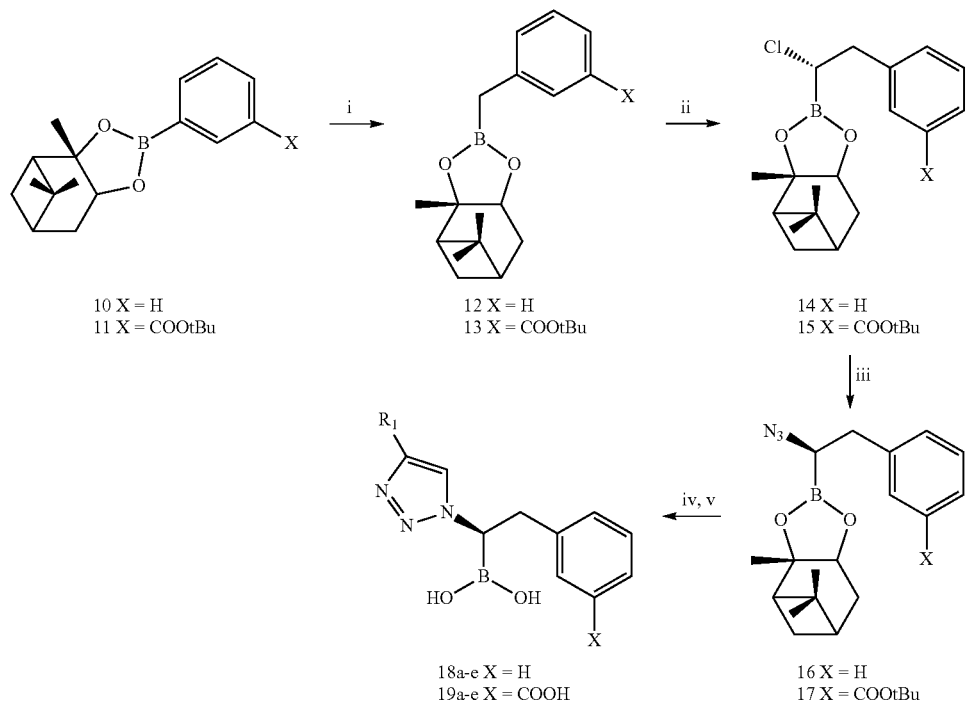

10 X = H
11 X = COOtBu

12 X = H
13 X = COOtBu

14 X = H
15 X = COOtBu 18a-e X = H
19a-e X = COOH

16 X = H
17 X = COOtBu (i) LiCH2Cl, THF, -80° C. → room temp.; (ii) LiCHCl2, THF, -100° C. → room temp.; (iii) NaN3, TBAHS, EtOAc, H2O, room temp.; (iv) alkyne, CuSO4, sodium ascorbate, tBuOH H2O, room temp.; (v) phenylboronic acid, HCl, acetonitrile, n-hexane, room temp.

(+)-Pinanediol boronates 10 and 11 were subjected to two consecutive homologation steps: the first with chloromethyllithium for methylene insertion to 12 and 13, and the second with dichloromethyllithium to introduce the halogenated carbon atom (14 and 15). Chlorine substitution with sodium azide under phase transfer conditions afforded 16 and 17. These key azido intermediates were then subjected to click reaction and deprotection to triazolyl analogs of acyl-boroPhe 18a-18e and 19a-19e (Table 2, Entries 6-15).

The results reported in Table 2 indicate that the described procedure is reproducible and highly efficient, and affords, in all cases, the expected triazolylmethylboronic acid in moderate to good overall yields as pure and stable solids, which can be stored for months at +4° C. The rate of the CuAAC reaction is not affected by the structure of the azidomethylboronate, but only by the electronic density of the alkyne partner: for a given alkyne, reaction times are consistent for both primary (intermediate 2) and secondary azides (intermediates 16 and 17). Furthermore, for these latter derivatives cycloaddition reaction proceeds without any change in the diastereoisomeric composition, to eventually afford enantiomerically pure triazolylmethylboronic acids.

Example 2

Compounds of general formula I can be prepared according to the procedures shown schematically in below.

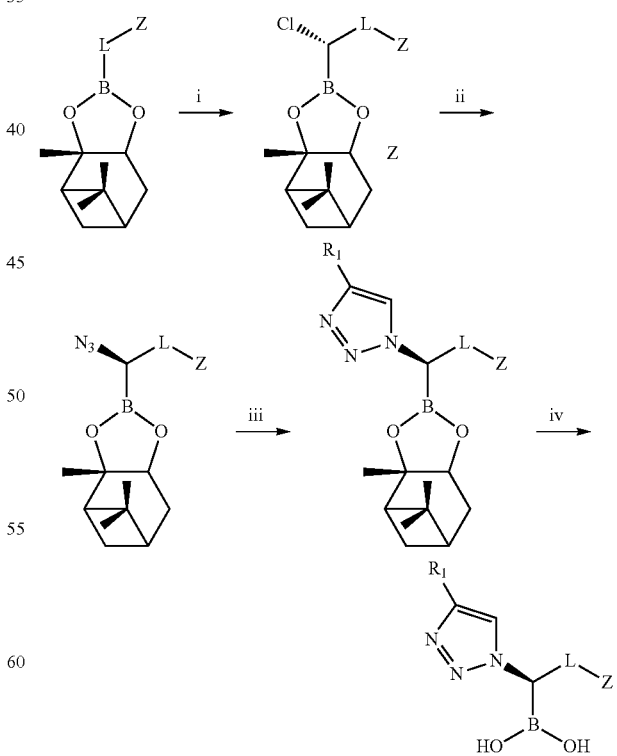

Particularly preferred embodiments relate to compounds of the formula 1a-e

1a
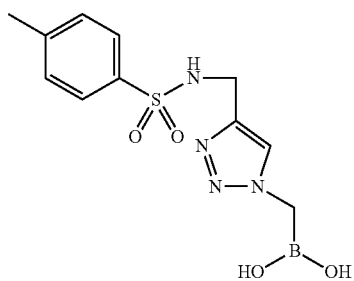

1b
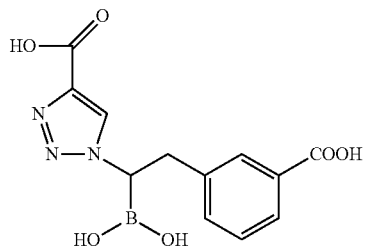

And to compounds:

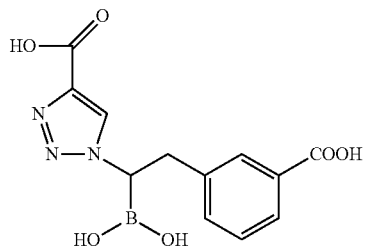
2a

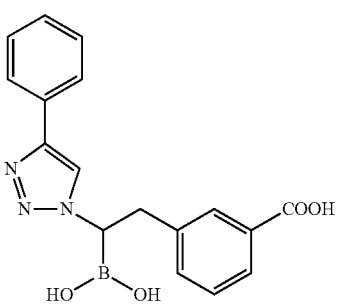
2b

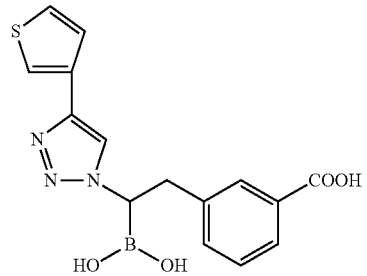
2c

1c
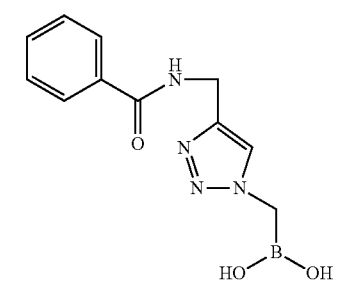

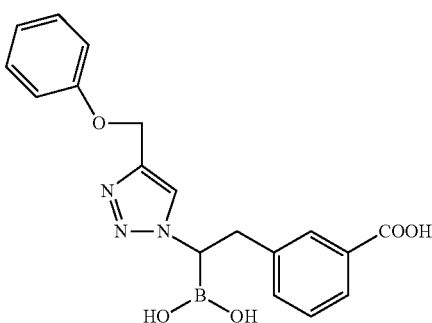
2d

1d
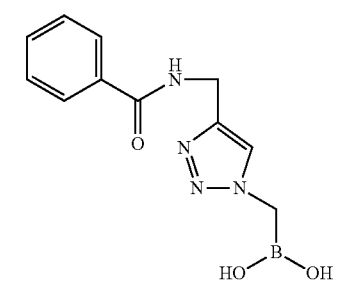

1e
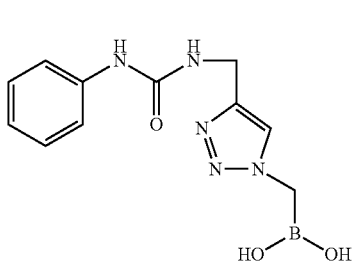

In Vitro Antibacterial Assays

To determine the ability of the compounds to inhibit the growth of bacterial strains when partnered with a β-lactam antibiotic the following assay was performed:

1.51 µl of an overnight culture of *E. coli* DH10B or DC-2 (hyperpermeable strain) harboring cloned b-lactamase (KPC-2, ADC-7, PDC-3) in pBCSK-expression vector was added to 1 ml Mueller-Hinton (MH) broth containing a concentration of antibiotic (imipenem, IMI or ceftazidime, CTZ) equal to one serial dilution less than the MIC. 1.5 µl of culture was also added to 1 ml MH broth containing antibiotic and 1001 µg compound (1a, b, c, d, e). As a control, 100 µg compound was added alone to *E. coli* DH10B. These cultures were grown for 7 hrs (220 rpm, 37° C.) and plated on MH agar at a dilution of 1:1000. The plates were incubated overnight and observed for colony formation. The results are shown in FIG. 1.

IC$_{50}$ Assays

IC$_{50}$ assays were performed to determine compound ability to inhibit enzyme. The inhibitor concentration which resulted in 50% reduction in nitrocefin (50 μM) hydrolysis after 5 min of pre-incubation of the enzyme and inhibitor at 25° C. is denoted as IC$_{50}$.

| | | IC$_{50}$ (μM) vs MBL | | | | IC$_{50}$ (μM) vs SBL | | | |
|---|---|---|---|---|---|---|---|---|---|
| Cmp | Structure | IMP-1* | NDM-1* | VIM-2* | VIM-24* | KPC-2** | ADC-7** | PDC-3** | OXA-23*** |
| 1a | 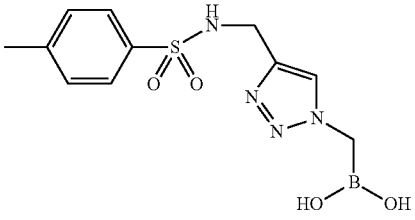 [SMILES: Cc1ccc(S(=O)(=O)NCc2cn(CB(O)O)nn2)cc1] | >100 | >100 | >100 | >100 | 1.3 ± 0.1 | 24 ± 3 | 9 ± 1 | >100 |
| 1b | 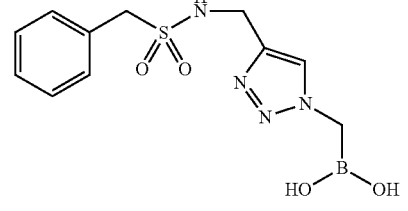 | >100 | >100 | 51 ± 5 | >100 | 4.2 ± 0.8 | 14.3 ± 1.4 | 4.5 ± 0.5 | >100 |
| 1c | 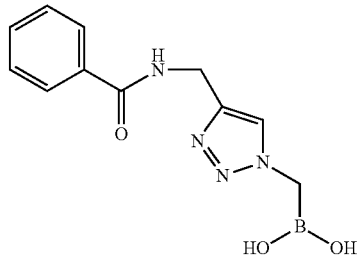 [SMILES: O=C(NCc1cn(CB(O)O)nn1)c1ccccc1] | >100 | >100 | 55 ± 5 | >100 | 10.8 ± 1.5 | 23 ± 3 | 26 ± 3 | >100 |
| 1d | 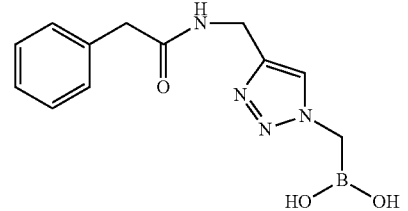 [SMILES: O=C(Cc1ccccc1)NCc1cn(CB(O)O)nn1] | >100 | >100 | 92 ± 9 | >100 | 12 ± 1 | 39 ± 4 | 23 ± 3 | >100 |
| 1e | 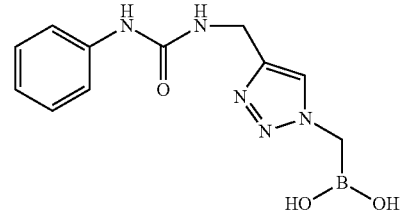 [SMILES: O=C(NCc1cn(CB(O)O)nn1)Nc1ccccc1] | >100 | >100 | 39 ± 4 | >100 | 5.2 ± 0.2 | 14 ± 2 | 10 ± 1 | >100 |

Buffers for IC$_{50}$ determination:

*10 mM HEPES, pH 7.5

200 mM NaCl 50 uM Zn2SO$_4$ 50 ug/ml BSA

**10 mM phosphate-buffered saline, pH 7.4

***50 mM Na Phosphate buffer, pH 7.2 (supplemented withy 20 mM Na bicarbonate)

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

Having described the invention, the following is claimed:

1. A method of treating a beta-lactam resistant bacterial infection in a subject in need thereof, the method comprising: administering to the subject therapeutically effective amounts of at least one β-lactam antibiotic and at least one triazolylmethyl boronic acid, wherein the triazolylmethyl boronic acid is selected from the group consisting of:

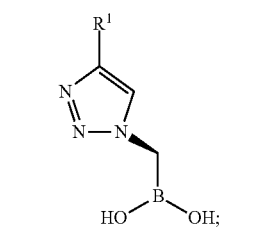
(III)

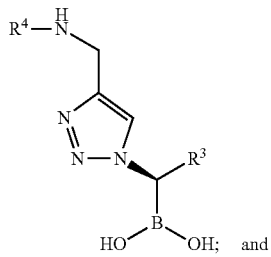
(IV)

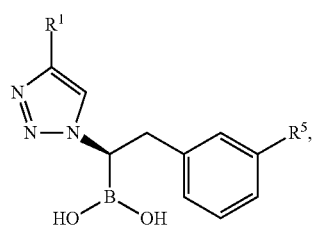
(V)

wherein $R^1$=CH$_2$NHC(=O)-phenyl or benzyl, CH$_2$NHS(=O)2-phenyl or alkyl substituted phenyl, —COOH, ester, aryl, heteroaryl, or —CH$_2$Oaryl;

$R^3$=benzyl, alkyl, H or —CH$_2$-benzoic acid;

$R^4$=S(=O)2-phenyl or alkyl substituted phenyl, C(=O)-phenyl or benzyl, C(=O)NH-phenyl;

$R^5$=—COOH or H; and pharmaceutically acceptable salts thereof.

2. The method of claim 1, wherein the triazolylmethyl boronic acid is selected from the group consisting of:

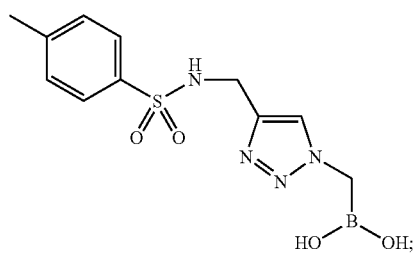

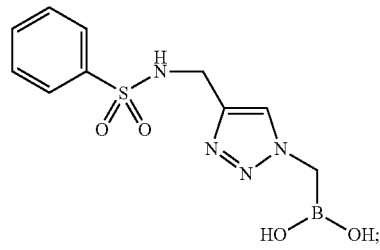

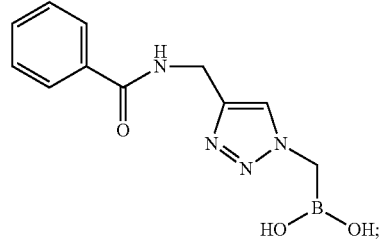

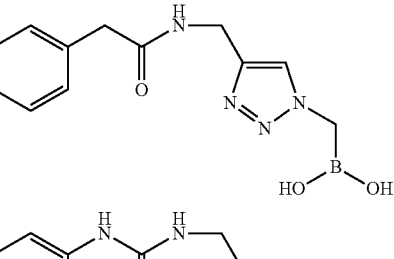

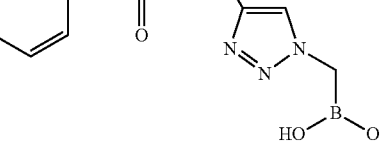

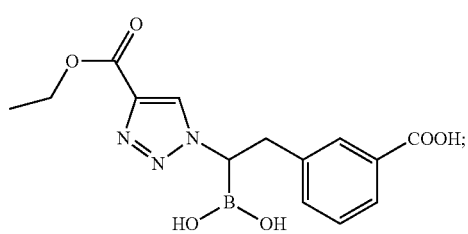

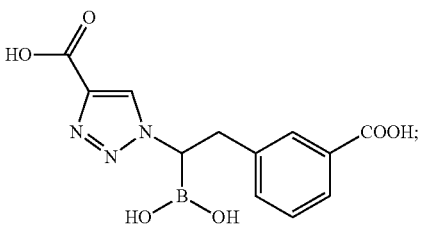

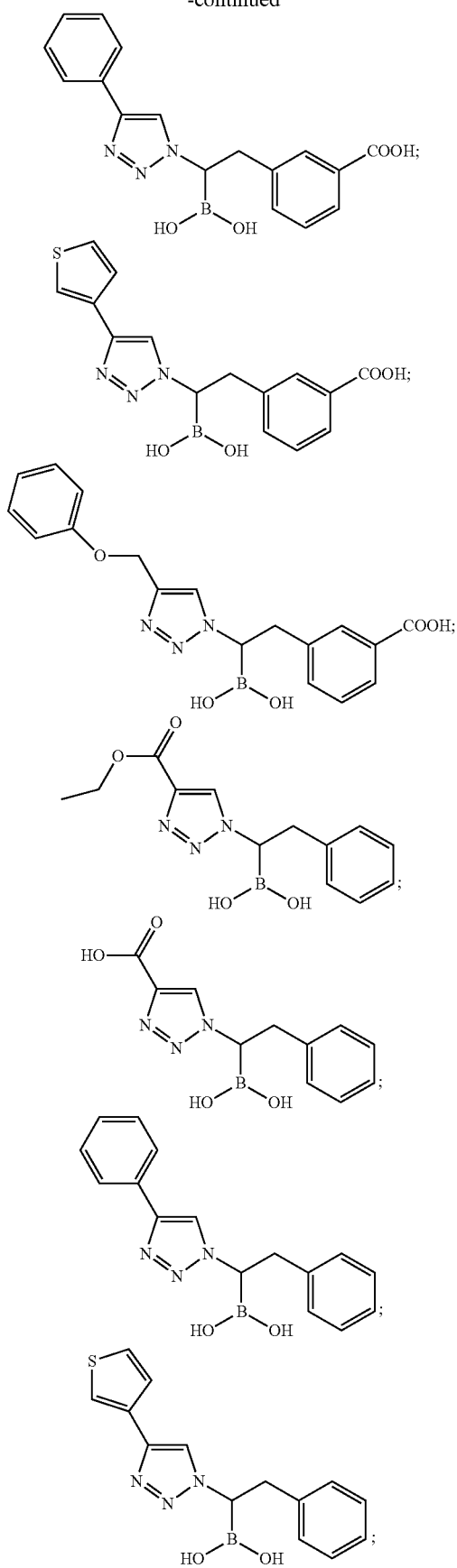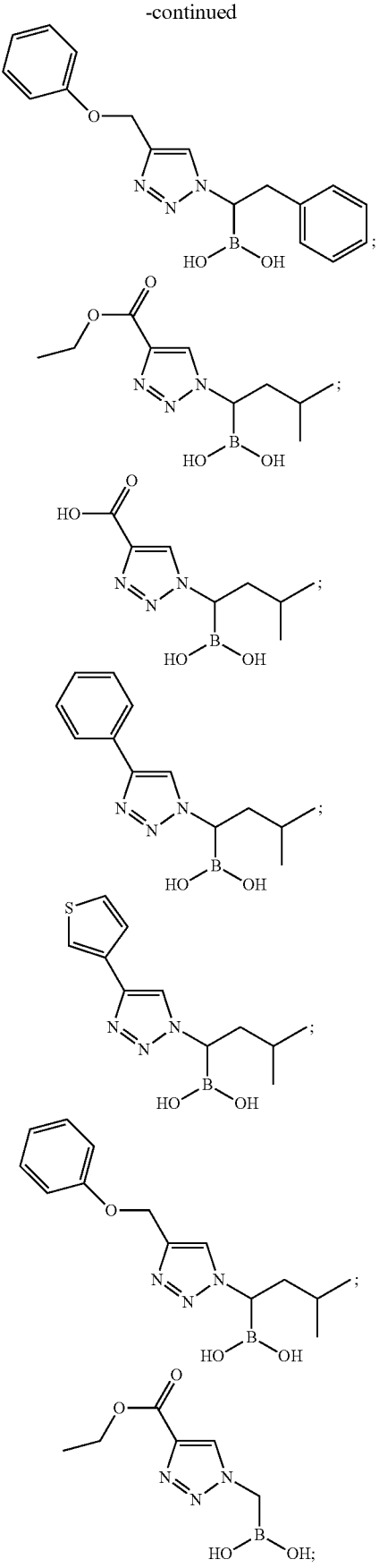

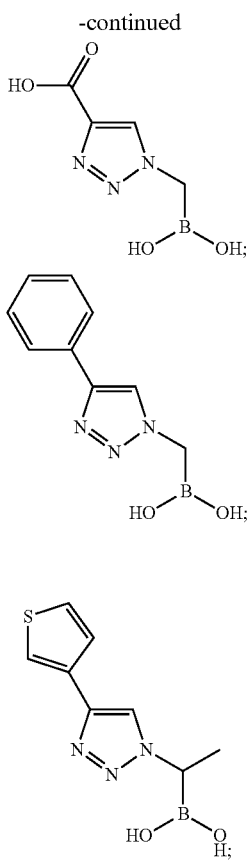

and pharmaceutically acceptable salts thereof.

3. The method of claim 1, wherein the β-lactam antibiotic is selected from the group consisting of amoxicillin, ampicillin, azlocillin, mezlocillin, hetacillin, bacampicillin, carbenicillin, sulbenicillin, ticarcillin, piperacillin, mecillinam, methicillin, ciclacillin, oxacillin, cloxacillin, dicloxacillin, nafcillin, cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, cefmenoxime, cefmetazole, cephaloglycin, cefonicid, cefodizime, cefpirome, ceftazidime, ceftriaxone, cefpiramide, cefozopran, cefepime, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbacef, latamoxef, ceftolozane (also referred to as FR-264,205 or CXA-101), imipenem, meropenem, biapenem, panipenem, ertapenem, doripenem, aztreonam, carumonam, and pharmaceutically acceptable salts.

* * * * *